(12) United States Patent
Eidenschink et al.

(10) Patent No.: US 8,291,570 B2
(45) Date of Patent: Oct. 23, 2012

(54) METHODS FOR ABLUMINALLY COATING MEDICAL DEVICES

(75) Inventors: Tracee E. J. Eidenschink, Wayzata, MN (US); Matt Heidner, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1181 days.

(21) Appl. No.: 12/130,846

(22) Filed: May 30, 2008

(65) Prior Publication Data

US 2009/0299452 A1 Dec. 3, 2009

(51) Int. Cl.
   *B21D 39/00* (2006.01)
   *A61F 2/06* (2006.01)

(52) U.S. Cl. ........... 29/458; 29/460; 29/508; 29/516; 29/517; 29/527.2; 29/283.5; 72/402; 427/2.24

(58) Field of Classification Search .......... 29/458, 29/460, 508, 516, 517, 527.2, 283.5; 72/402; 427/2.24
   See application file for complete search history.

(56) References Cited

U.S. PATENT DOCUMENTS

| | | |
|---|---|---|
| 5,913,871 A | 6/1999 | Werneth et al. |
| 6,360,577 B2 | 3/2002 | Austin |
| 6,568,235 B1 | 5/2003 | Kokish |
| 6,651,478 B1 | 11/2003 | Kokish |
| 6,823,576 B2 | 11/2004 | Austin |
| 6,840,081 B2 | 1/2005 | Kokish |
| 6,915,560 B2 | 7/2005 | Austin |
| 6,958,073 B2 | 10/2005 | Rogers et al. |
| 6,986,785 B2 | 1/2006 | O'Shaughnessy et al. |
| 7,021,114 B2 | 4/2006 | Perreault |
| 7,143,625 B2 | 12/2006 | Edin |
| 7,225,518 B2 * | 6/2007 | Eidenschink et al. ....... 29/283.5 |
| 7,309,349 B2 | 12/2007 | Jackson et al. |
| 7,487,579 B2 * | 2/2009 | Eidenschink et al. .......... 29/515 |
| 2002/0049492 A1 | 4/2002 | Lashinski et al. |
| 2004/0193177 A1 | 9/2004 | Houghton et al. |
| 2005/0154450 A1 * | 7/2005 | Larson et al. ................ 623/1.42 |
| 2006/0004469 A1 * | 1/2006 | Sokel ............................ 623/909 |

FOREIGN PATENT DOCUMENTS

| | | |
|---|---|---|
| EP | 1466570 | 10/2004 |
| WO | 0121103 | 3/2001 |

* cited by examiner

*Primary Examiner* — Jermie Cozart

(74) *Attorney, Agent, or Firm* — Seager Tufte & Wickhem LLC

(57) ABSTRACT

A stent crimping and coating apparatus is disclosed. The apparatus includes a plurality of crimping blades positioned in a radial array and collectively forming a central crimping lumen, wherein the plurality of crimping blades radially movable to alter the diameter of the central crimping lumen. Each of the crimping blades includes a first surface configured to at least in part define the central crimping lumen. One or more of the crimping blades includes a fluid channel extending therein and a plurality of openings in fluid communication with the fluid channel. The plurality of openings are located at the first surface of the one or more crimping blades and adapted to discharge a fluid into the central crimping lumen.

13 Claims, 24 Drawing Sheets

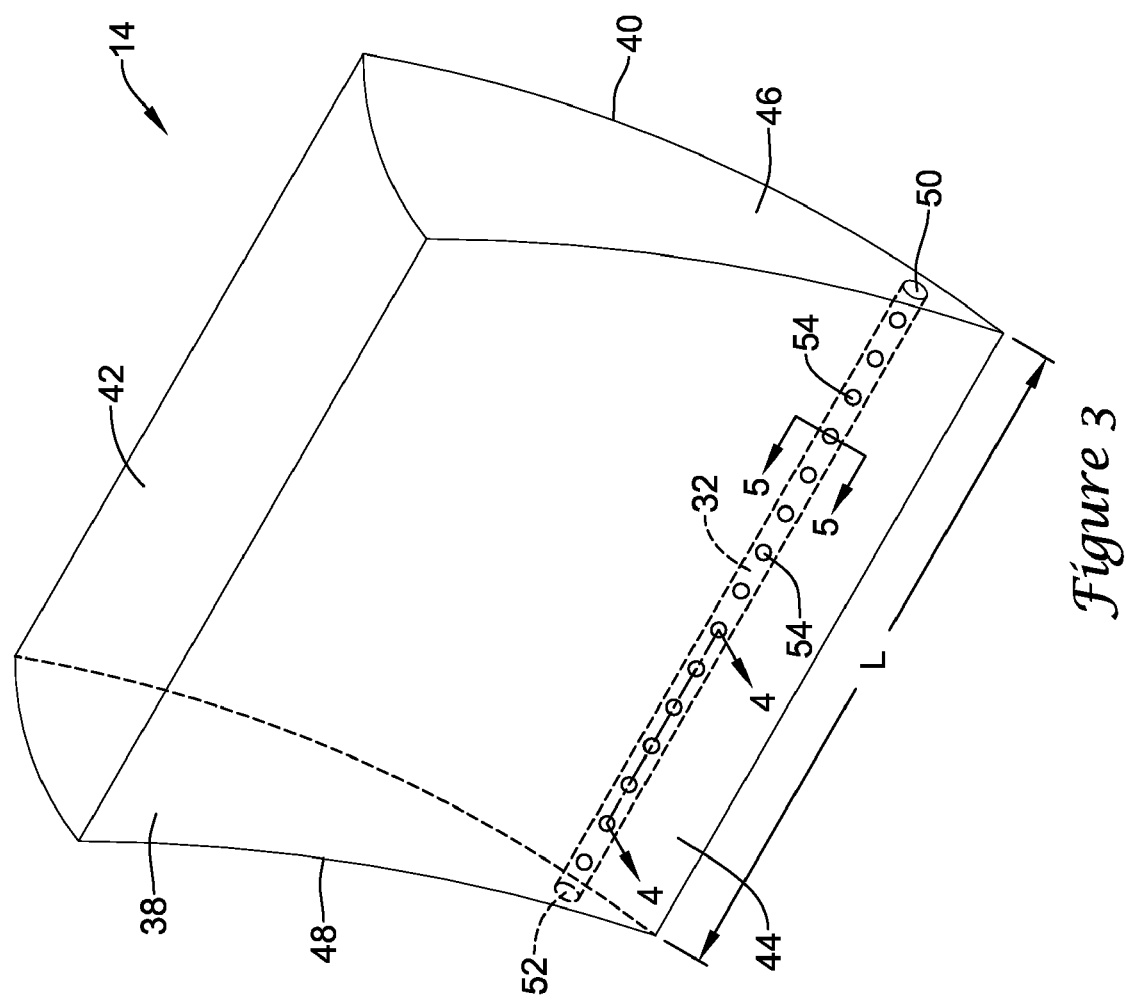

METHODS FOR ABLUMINALLY COATING MEDICAL DEVICES

FIELD

The present disclosure relates generally to the field of coating and crimping stents or other medical devices. More specifically, the present disclosure pertains to apparatus and methods for abluminally coating stents or other medical devices mounted onto a delivery device.

BACKGROUND

Medical devices such as stents, stent grafts, and vena cava filters are often utilized in combination with a delivery device for placement at a desired location within the body. A medical prosthesis such as a stent, for example, may be loaded onto a stent delivery device such as a balloon catheter and then introduced into the lumen of a body vessel in a configuration having a reduced diameter. Once delivered to a target location within the body, the stent may then be expanded to an enlarged configuration within the vessel to support and reinforce the vessel wall while maintaining the vessel in an open, unobstructed condition. In some medical procedures such as a percutaneous transluminal coronary angioplasty (PTCA), for example, the stent may be deployed and expanded within a vessel adjacent to the location where a lesion has been removed to prevent restenosis or prolapse of the vessel at that region. The stent may be either self-expanding, or alternatively, may be manually expanded by the inflation of a balloon on the delivery device.

Inflation expandable stents are typically secured to the balloon catheter in a reduced diameter configuration or profile prior to their use. In some techniques, for example, the stents are loaded onto the balloon and then inserted into a crimping device which applies an inwardly directed radial force to the stent. In some techniques, the balloon may be heated to a temperature above the glass transition temperature of the balloon material, causing the balloon material to flow and attach or mold to the stent material. In some embodiments, an adhesive material having a melt point below that of the balloon material may also be used in some cases to further adhere the stent to the outer surface of the balloon.

The coating of stents is often performed in a separate step prior to being crimped onto the balloon catheter. In some techniques, for example, the entire surface of the stent may be coated by placing the stent in a dip bath containing a drug coating material such as Rapamycin or Heparin. Once coated, the stent is then crimped onto the balloon catheter in a later step using a combination of pressure and heat. In some cases, the application of pressure to the stent during the crimping process may interfere with the drug coating material. The loading of the stent onto the balloon catheter may result in frictional forces exerted on the stent that can cause damage to the underlying coating on the stent, in some cases resulting in chipping of the drug coating. The application of heat to the stent may also cause changes in the chemical composition of the drug coating material and may create thermal cracks in the coating, limiting the types of drug coatings that can be used. Accordingly, there is a need for new apparatuses and methods for coating and crimping medical devices onto delivery devices.

BRIEF SUMMARY

The present disclosure pertains to apparatus and methods for abluminally coating stents or other medical devices mounted onto a delivery device. An illustrative crimping apparatus can include a number of movable crimping blades forming an aperture for receiving a medical device such as a stent. One or more of the crimping blades can include a fluid channel in fluid communication with a fluid reservoir. During crimping, a number of openings in the blades can be used to abluminally deliver fluid onto the medical device. In some embodiments, for example, the openings in the blade can be utilized to spray or extrude a drug coating material onto the stent during the crimping process.

An illustrative method of coating a medical device can include providing a crimping apparatus including a plurality of crimping blades positioned in a radial array and collectively forming a central crimping lumen. The plurality of crimping blades is radially movable to alter the diameter of the central crimping lumen. One or more of the crimping blades includes a fluid channel extending therein and a plurality of openings in fluid communication with the fluid channel. A balloon of a balloon catheter and a stent surrounding a portion of the balloon may be positioned in the crimping lumen of the crimping apparatus. The plurality of crimping blades may be radially contracted toward the stent to thereby crimp the stent onto the balloon. At least a portion of the stent may be coated with a fluid by discharging a fluid into the crimping lumen and into contact with the stent from the plurality of openings. The plurality of crimping blades may be radially retracted away from the stent, and the balloon and crimped stent may be removed from the crimping lumen of the crimping apparatus.

BRIEF DESCRIPTION OF THE DRAWINGS

FIG. 3 is a perspective view showing an illustrative crimping blade having a number of openings along its length;

DETAILED DESCRIPTION

The following detailed description should be read with reference to the drawings. The drawings, which are not necessarily to scale, depict illustrative embodiments and are not intended to limit the scope of the disclosure. Although examples of construction, dimensions, and materials are illustrated for the various elements, those skilled in the art will recognize that many of the examples provided have suitable alternatives that may be utilized. Moreover, while the illustrative apparatuses and methods are described with respect to the coating of stents and crimping of stents onto a balloon of a stent delivery catheter, it should be understood that other medical devices may benefit from one or more of the features disclosed herein. Examples of other medical devices can include, but are not limited to, grafts, stent-grafts, and vena-cava filters.

Figure 1:
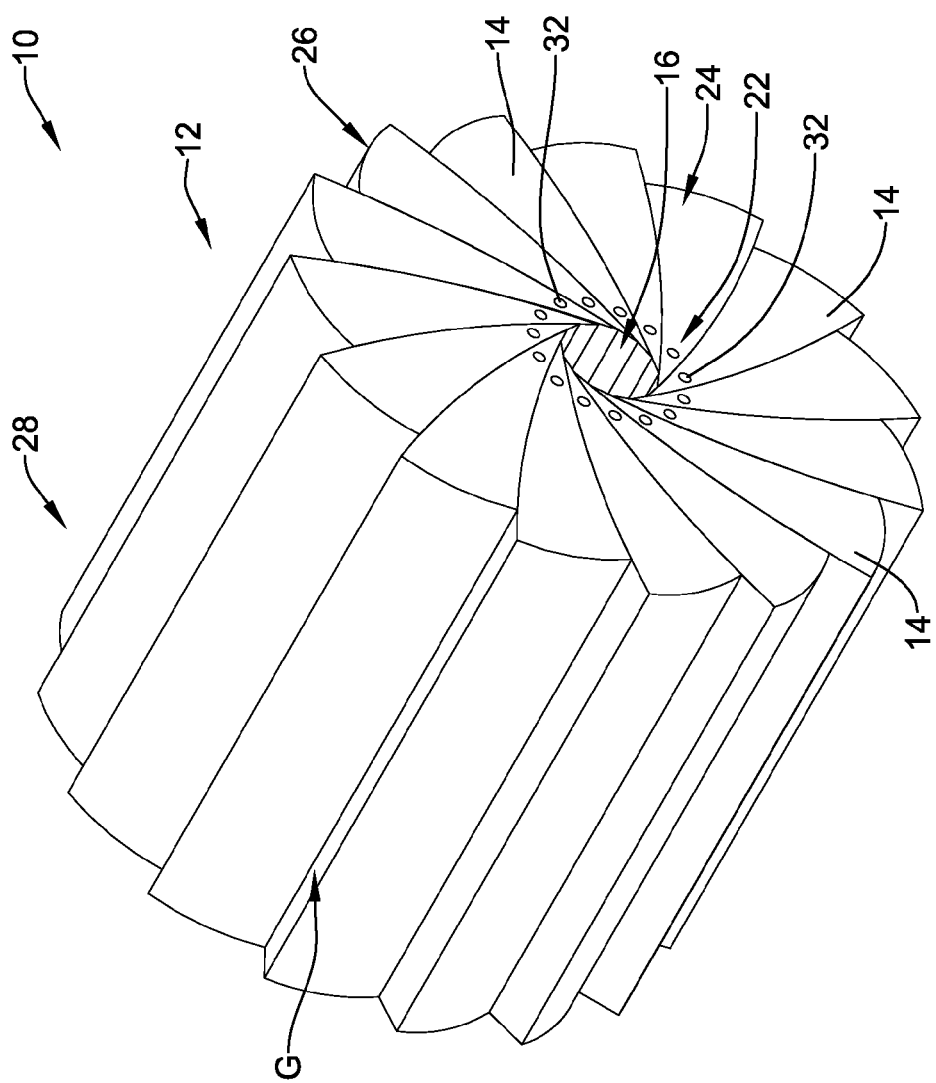
FIG. 1 is a perspective view of an illustrative apparatus for crimping and coating a medical device.

Referring now to FIG. 1, an illustrative crimping apparatus 10 in accordance with an illustrative embodiment will now be described. The crimping apparatus 10, illustratively a stent crimping and coating apparatus for crimping a stent onto the balloon of a balloon delivery catheter, can include a crimping section 12 having a number of movable blades 14 radially disposed about a central crimping lumen 16. In the illustrative embodiment depicted in FIG. 1, for example, the crimping section 12 includes fifteen blades radially disposed about the lumen 16. The crimping apparatus 10 may be equipped with a greater or lesser number of crimping blades 14, however, depending on the size and configuration of the stent to be inserted therein. The crimping blades 14 may be made of a suitably hard material such as a hardened steel or ceramic, although other materials are possible. The crimping blades 14 can be configured to move independently of each other or in unison, and can be configured to collectively contract inwardly towards the central axis of the crimping lumen 16 and retract outwardly away from the central axis of the lumen 16 in order to adjust the size of the crimping lumen 16. When contracted, each of the crimping blades 14 can be configured to provide an inwardly directed radial force to the inserted stent assembly disposed in the crimping lumen 16. Movement of the crimping blades 14 can be accomplished using an actuation mechanism (not shown), which can include a number of levers, cams, bearings, connecting links, rods, motors, gears, or the like. In use, the crimping apparatus 10 may be used to reduce the diameter of a stent inserted within the crimping lumen 16 and/or may be used to crimp the stent onto another member such as a balloon delivery catheter or introducer.

In some embodiments, the crimping apparatus 10 may be equipped with a loading platform (not shown) that can be used to facilitate the insertion of the stent and stent delivery catheter into the crimping lumen 16 during crimping and, in some cases, coating. The platform may be configured to support the stent and/or stent delivery catheter during loading of the assembly into the crimping lumen 16 for crimping. In some embodiments, for example, the position of the platform can be adjusted to ensure that the stent and/or stent delivery catheter are loaded centrally within the crimping lumen 16. Such central loading may be beneficial, for example, to ensure that the radial forces exerted on the stent are substantially uniform during the crimping process.

Each of the crimping blades 14 can include an inner section 22 (e.g., a radially inward portion), a peripheral section 24 (e.g., a radially outward portion), and a length extending from a first end 26 of the apparatus 10 to a second end 28 thereof. The crimping blades 14 may be arranged about a reference circle to form an adjustable crimping aperture, such as an iris. In some embodiments, the crimping blades 14 can be configured and arranged such that each blade 14 has only a single point which lies on the circumference of the reference circle prior to movement of the blade and is moved along a radius of the reference circle upon movement of the blade 14.

The crimping blades 14 may have a length that is equal to or greater than the length of the stent to be inserted into the crimping lumen 16. In some embodiments, for example, the length of the crimping blades 14 may be about 5 cm to 20 cm in length, and more specifically, about 10 cm to 15 cm in length. The length of the crimping blades 14 may deviate from these dimensions, however, depending on the particular configuration of the stent or other medical device to be crimped, the length of crimping desired, as well as other factors. Typically, the crimping blades 14 will have a length as long as or longer than the medical device (e.g., stent) positioned in the crimping lumen 16 such that the medical device is reduced uniformly in size along its length. In crimping stents, for example, the blades 14 will typically have a length at least as long as the axial length of the stent, thus ensuring a more uniform crimp along the length of the stent.

The crimping blades 14 may be separated from each other by a small gap G, which may extend along the entire length of the blade 14. In use, the small gap G between each of the blades 14 allows the blades 14 to slide relative to each other. In certain embodiments, the gap G can be configured so that the blades 14 slide relative to one another without an undue amount of friction. The amount of spacing G between the crimping blades 14 may depend upon several factors, including the number of blades 14, the size and shape of the blades 14, the desired size of the crimping lumen 16, and the size of the stent assembly.

The crimping lumen 16 may extend longitudinally along an axis from the first end 26 of the apparatus 10 to the second end 28 thereof. Alternatively, and in other embodiments, the crimping lumen 16 may extend longitudinally from the first end 26 of the apparatus 10 toward the second end 28 but terminate before the second end 28.

Figure 2:
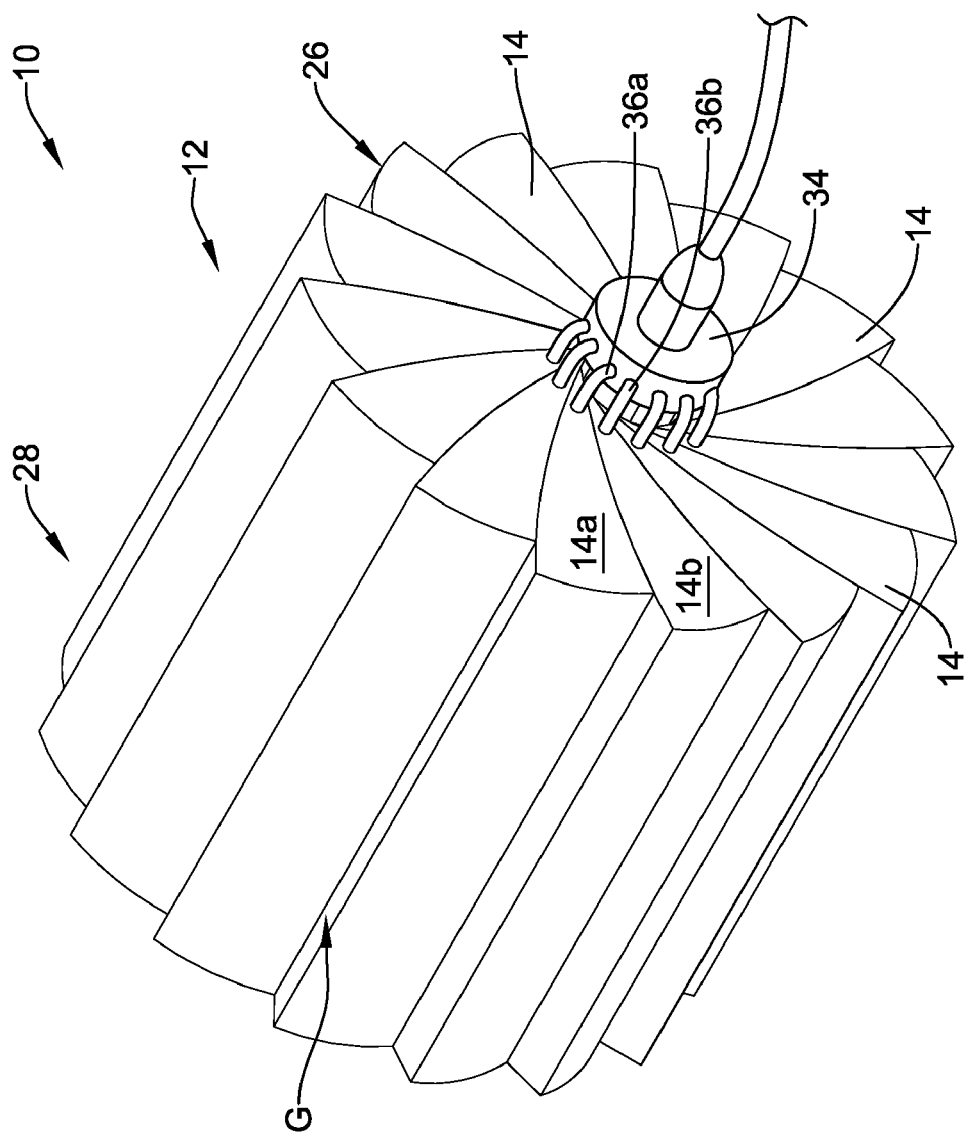
FIG. 2 is a perspective view of the apparatus of FIG. 1 including a manifold for distributing a fluid to the crimping blades.

The inner section 22 of each of the crimping blades 14 may include one or more fluid channels 32 that can be connected to a fluid reservoir containing a drug coating material, lubricious material, adhesive, bonding material, and/or other desired material. In some embodiments, the supply of fluid to the fluid channels 32 can be accomplished via a fluid manifold, which can be connected to one or both ends 26,28 of the crimping apparatus 10. As shown further in FIG. 2, for example, a fluid manifold 34 can be coupled to or formed integrally with an end 26 of the crimping apparatus 10 for providing pressurized fluid (e.g., liquid, gel, gas) to one or more of the fluid channels 32.

The fluid manifold 34 can include a number of fluid conduits 36 each adapted to supply fluid to a particular fluid channel 32 or group of channels 32. The number and configuration of the fluid conduits 36 may differ, however, from that shown in FIG. 2. For example, although a separate fluid conduit 36 is shown connected to each of the fluid channels 32, a single fluid conduit 36 can be connected to the fluid channels 32 for multiple crimping blades 14. In one alternative embodiment, for example, each alternating fluid channel 32 can be coupled to a first fluid conduit 36a for supplying a first fluid to a first blade 14a whereas a second fluid conduit 36b may be used for supplying a second fluid or gas to another blade 14b. Other configurations are possible, however. The fluid manifold 34 may include a number of valves that each can be selectively opened or closed to deliver pressurized fluid (e.g., liquid, gel, gas) to selective crimping blades 14. In some embodiments, for example, a MEMS valve, solenoid valve, or roller-ball valve may be activated on the fluid manifold 34 to provide pressurized fluid to one or more crimping blades, as desired.

FIG. 3 is a perspective view showing a crimping blade 14 in accordance with an illustrative embodiment having a number of fluid openings along its length. As shown in FIG. 3, each of the crimping blades 14 may have a wedge shape defined by a first side 38, a second side 40, a peripheral portion 42, and a tip 44. The first and second sides 38,40 of the crimping blade 14 can be curved slightly so as to form a substantially circular shaped lumen 16 when the blades 14 are extended in a fully closed position. However, in other embodiments the shape of the crimping blade 14 may differ from that depicted in FIG. 3.

The fluid channel 32 may extend along all or a portion of the length L of the crimping blade 14 from a first end 46 of the blade 14 to a second end 48 thereof. As shown in FIG. 3, for example, the fluid channel 32 may extend from a first aperture 50 on the first end 46 of the blade 14 through the entire length L of the blade 14, terminating in a second aperture 52 located on the second end 48 of the blade 14. In this configuration, the second aperture 52 may be fluidly coupled to another (e.g., return) fluid manifold, allowing fluid to be recirculated. Such a configuration may be useful in some embodiments, for example, to ensure a more uniform pressure differential across the fluid channel 32 to the pressure losses within the channel 32. Alternatively, and in other embodiments, the fluid channel 32 may extend along only a portion of the length L of the crimping blade 14, terminating within the interior of the blade 14.

A number of openings 54 located along the length of the crimping blade 14 and adjacent to the fluid channel 32 can be utilized to spray, extrude, weep, leak, perfuse, or otherwise deliver pressurized fluid from within the channel 32 onto the outer surface of the stent and the stent delivery device. The openings 54 can be provided at a location at or near the tip 44 of the crimping blade 14 where contact is made with the inserted stent. In the illustrative embodiment of FIG. 3, the openings 54 are disposed at uniform intervals along all or a portion of the length L of the blade 14. The uniform spacing of the openings 54 allows fluid to be more uniformly applied along the length of the stent. It should be understood, however, that the number and spacing of the openings 54 may vary from that shown. For example, in some embodiments the openings 54 may be non-uniformly spaced along at least a portion of the length of the blade 14.

Figure 4A:
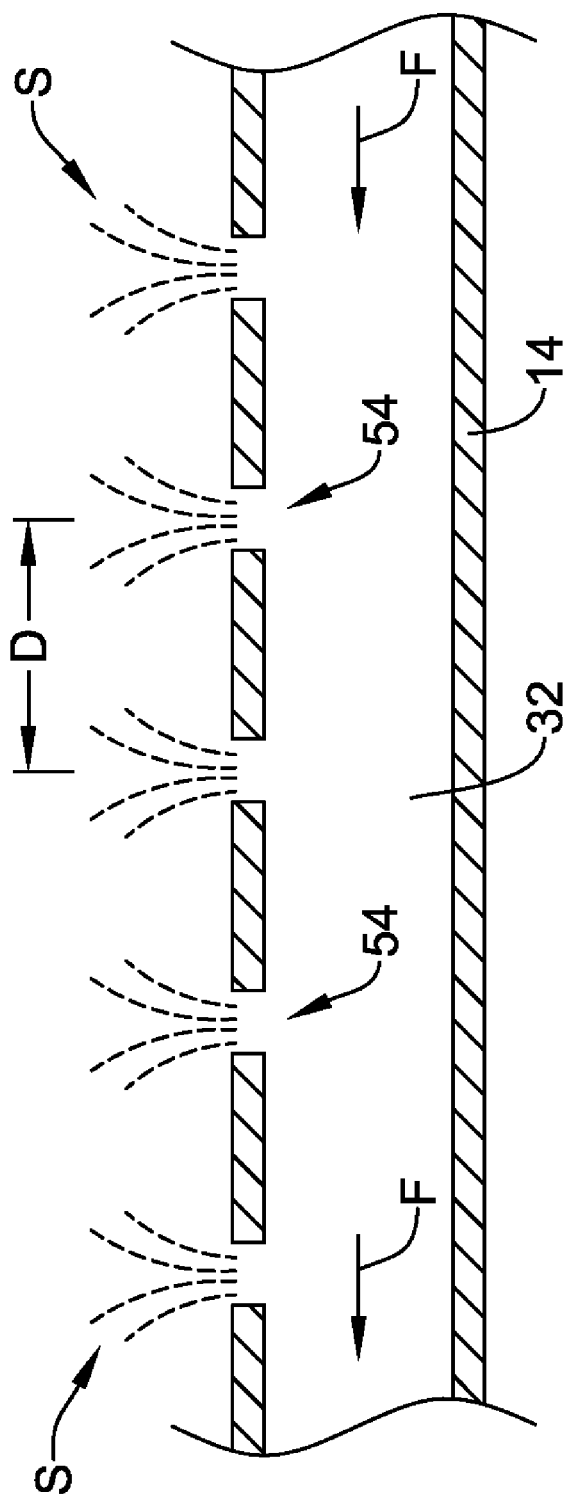
FIG. 4A is a side cross-sectional view showing the crimping blade of FIG. 3 along line 4-4.

FIG. 4A is a side cross-sectional view showing the crimping blade 14 along line 4-4 in FIG. 3. As shown further in FIG. 4A, each of the openings 54 may be spaced apart from each other by a distance D. In some embodiments, for example, the distance D between each opening 54 may be about 1 cm to about 3 cm, and more specifically about 2 cm. However, in other embodiments, the distance D between adjacent openings 54 may deviate from these expressed dimensions. During coating, and as further discussed herein, fluid F within the fluid channel 32 can be discharged through the openings 54 to coat the outer exposed portions of the stent and/or the stent delivery device. The pressure of the fluid F within the fluid channel 32 may vary depending on the viscosity of fluid F, the temperature of the fluid F, the transverse dimensions of the fluid channel 32, the length of the fluid channel 32, as well as other factors. In some embodiments, a relatively high pressure (e.g., above 100 psi) may be applied to the fluid channel 32 to produce an atomized spray S of fluid from each of the openings 54, as shown.

Figure 4B:
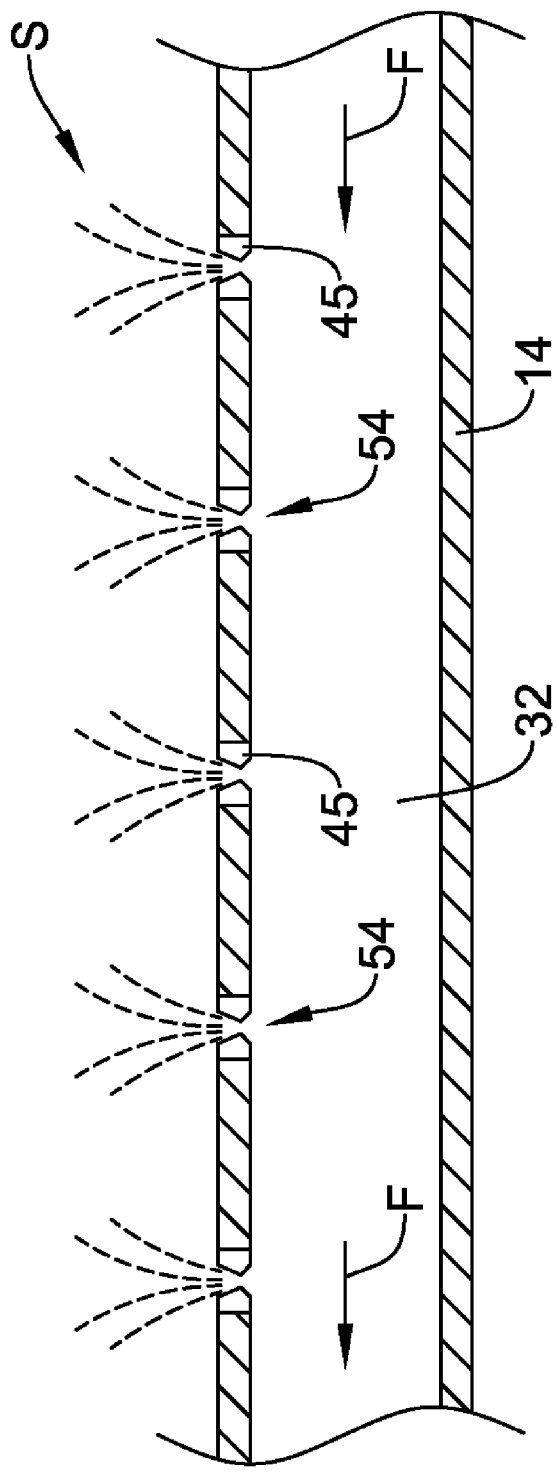
FIG. 4B shows an alternative embodiment of the crimping blade of FIG. 3 along line 4-4.

FIG. 4B is a side cross-sectional view showing an alternative embodiment of the crimping blade 14 along line 4-4 in FIG. 3. As shown further in FIG. 4B, each of the openings 54 may include a nozzle 45 positioned within the openings 54. The nozzles 45 may be chosen to control the characteristics of a fluid flow, such as flow rate, speed, direction and/or pressure, as the fluid exits the blade 14. For example, the nozzles 45 may be chosen to direct fluid in a desired pattern from the blade 14 during a crimping process. For instance, in some embodiments, a nozzle 45 may be chosen to provide a flat spray pattern, a conical spray pattern, or other desired spray pattern. The nozzles 45 may include an opening or orifice of varying cross-sectional area. For example, a convergent nozzle may include an opening which narrows from a larger diameter to a smaller diameter in the direction of fluid flow, whereas a divergent nozzle may include an opening which expands from a smaller diameter to a larger diameter in the direction of fluid flow. The nozzle 45 may also include a convergent section followed by a divergent section in the direction of fluid flow.

Figure 4C:
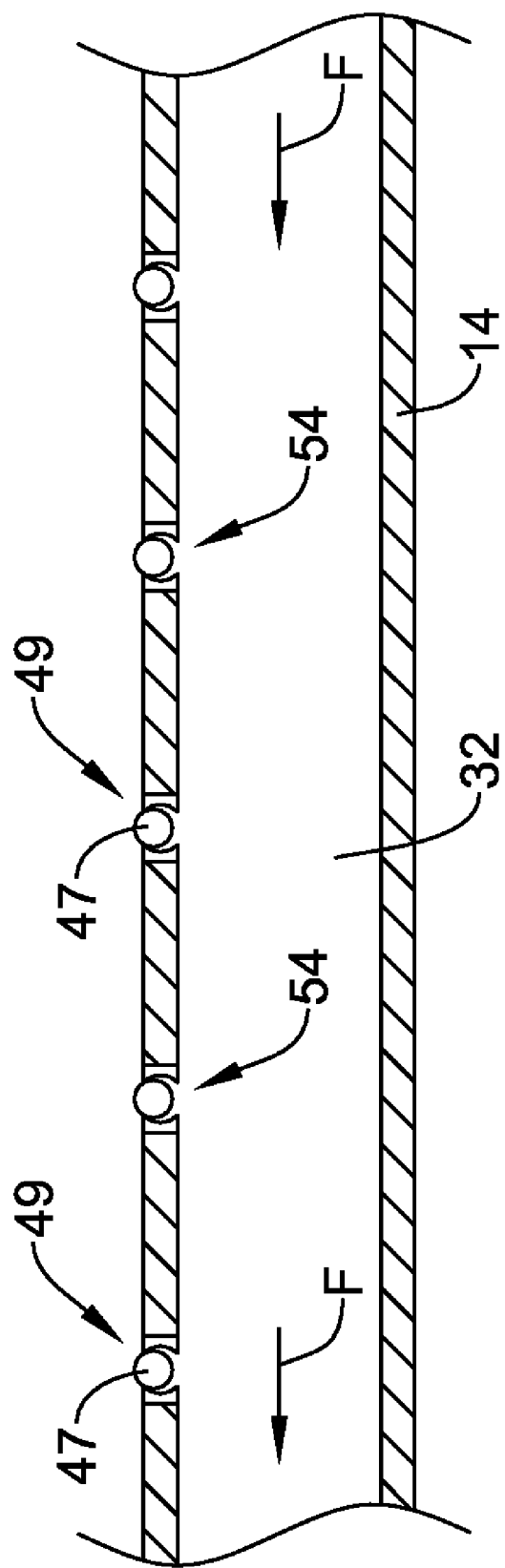
FIG. 4C shows an alternative embodiment of the crimping blade of FIG. 3 along line 4-4.

FIG. 4C is a side cross-sectional view showing an alternative embodiment of the crimping blade 14 along line 4-4 in FIG. 3. As shown further in FIG. 4C, each of the openings 54 may include a ball valve 49 including a ball 47 seated within each of the openings 54 of the blade 14. When the force exerted on the ball 47 by pressure within the channel 32 is greater than external forces exerted on the ball 47 from exterior of the channel 32, the ball 47 seats against the opening 54, preventing fluid from being discharged out of the channel 32. However, when a force is applied to the ball 47 exterior of the blade which is sufficient to unseat the ball 47 from the opening 54 (i.e., the applied force is greater than the force generated by the fluid pressure within the channel 32) fluid F may be expelled from the blade 14 past the ball 47. For example, during a crimping process, when the ball 47 comes into contact with a stent as the crimping blades are compressed down on the stent, the stent may force the balls 47 to become unseated, allowing the fluid F to flow out of the channel 32 and into contact with the stent. When the applied force is removed, or reduced, the ball 47 may again be seated against the opening 54, discontinuing the discharge of fluid F out of the channel 32.

Figure 5:
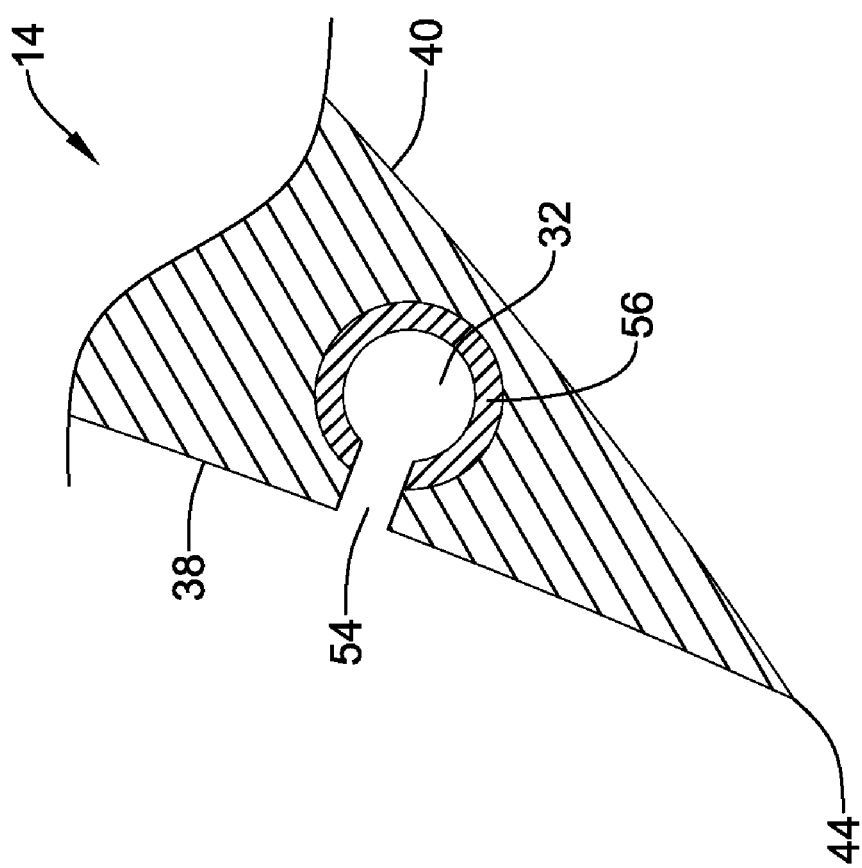
FIG. 5 is a transverse cross-sectional view showing the crimping blade of FIG. 3 along line 5-5.

FIG. 5 is a transverse cross-sectional view along line 5-5 in FIG. 3, showing the transverse shape of the fluid channel 32 and openings 54 in greater detail. As can be seen in FIG. 5, the fluid channel 32 may have a substantially circular or elliptical shape, and in some embodiments can comprise an insert 56 removably disposed within the interior of the crimping blade 14. The size of the opening 54 can be made smaller than the diameter of the fluid channel 32, forming a convergent/divergent nozzle that acts to throttle fluid pressure at the opening 54 in some instances. In certain embodiments, the opening 54 can be configured to produce a spray that exits the opening 54 at an angle sufficient to cover the entire length of the stent.

Figure 6:
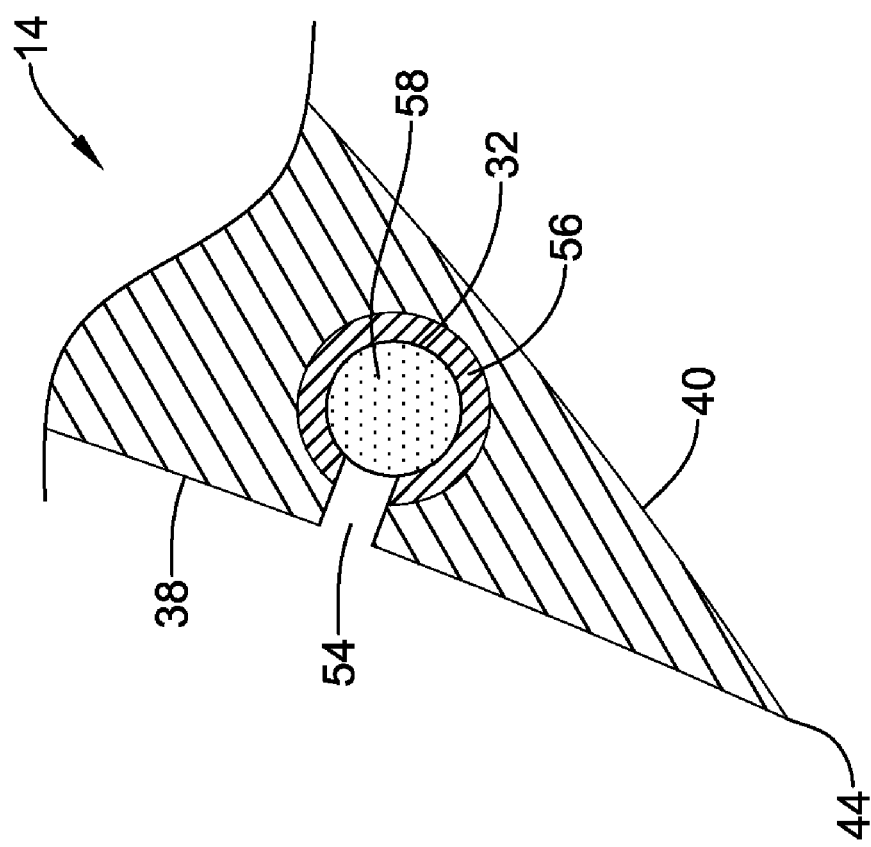
FIG. 6 is an alternative transverse cross-sectional view of the crimping blade of FIG. 3 along line 5-5 showing a sponge inserted into the fluid aperture.

In some embodiments, and as further shown in FIG. 6, the crimping blade 14 may further include a fluid permeable member 58 such as a sponge or other open celled structure disposed within the fluid channel 32 for storing fluid within the interior of the blade 14. The fluid permeable member 58 may extend along all or a portion of the length of the fluid channel 32, and can be configured to act as a storage reservoir for holding fluid within the crimping blade 14.

Figure 7:
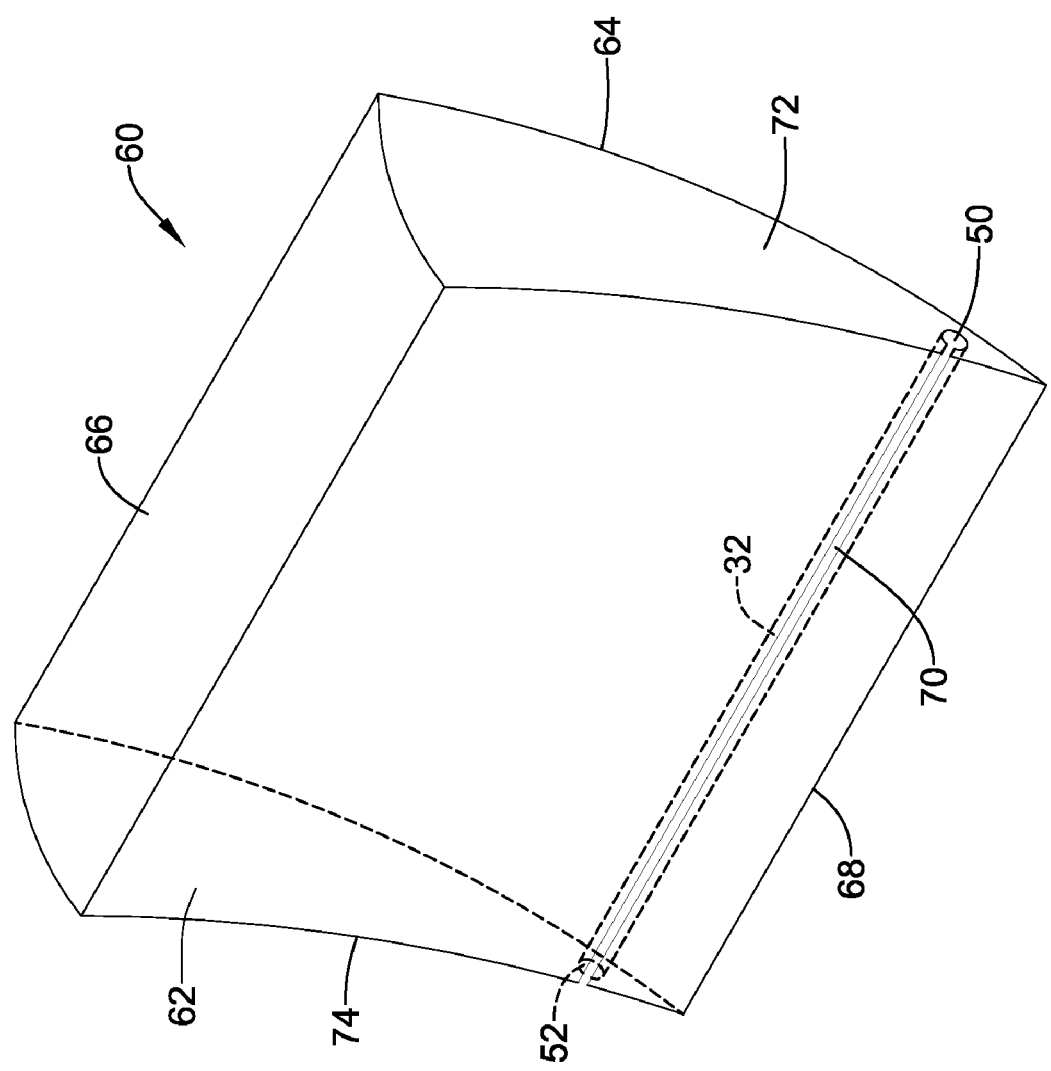
FIG. 7 is a perspective view showing another illustrative crimping blade having a slot formed along the length of the blade.

FIG. 7 is a perspective view showing another illustrative crimping blade 60 having a slot or slit 70 along the length of the blade 60. The crimping blade 60 may be shaped similar to the crimping blade 14 depicted in FIG. 3, having a wedge shape defined by a first side 62, a second side 64, a peripheral portion 66, and a tip 68. In the illustrative embodiment depicted, the slot or slit 70 may be a continuous slot or slit 70 formed through the first side 62 of the crimping blade 60 which may be configured to spray, extrude, weep, leak, perfuse, or otherwise deliver pressurized fluid to the stent and stent delivery device. The slot or slit 70 may extend along all or a portion of the length of the blade 60 from a first end 72 of the blade 60 to a second end 74 thereof. In some embodiments, the blade 60 may include two or more slots or slits 70 extending along a portion of the length of the blade 60. In some embodiments, the slot or slit 70 may extend substantially the entire length of the blade 60, except for at the extreme ends 72,74 of the blade 60. In some embodiments, the length of the slot or slit 70 (or the combined length of a plurality of slots or slits 70) may be about 60% or more, 70% or more, about 80% or more, about 90% or more, or about 95% or more of the length of the crimping blade 60.

Figure 8:
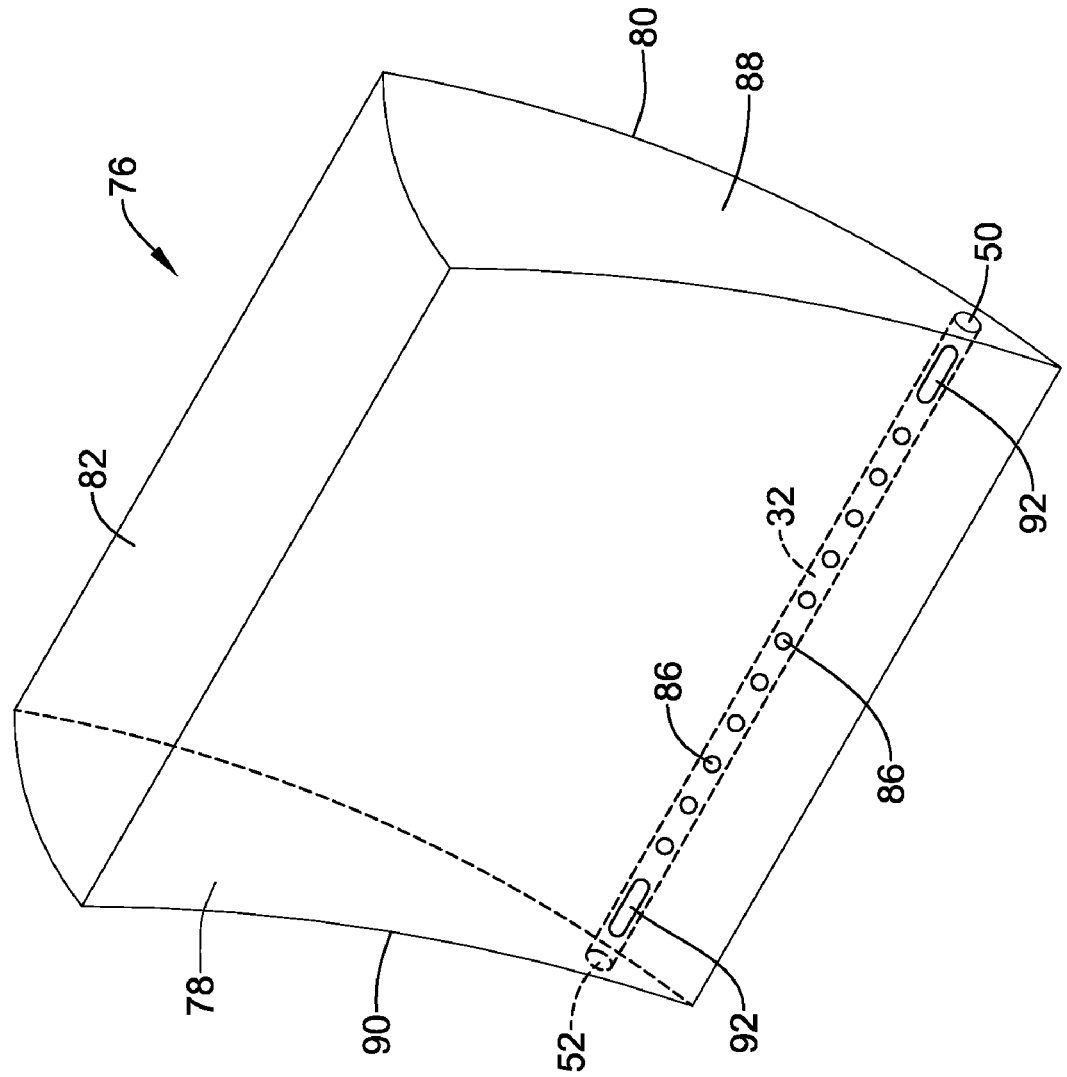
FIG. 8 is a perspective view showing another illustrative crimping blade having a number of larger openings located at opposing ends of the crimping blade.

FIG. 8 is a perspective view showing another illustrative crimping blade 76 having a number of larger openings disposed at each end of the blade 76. The crimping blade 76 may be shaped similar to the crimping blade 14 depicted in FIG. 3, having a wedge shape defined by a first side 78, a second side 80, a peripheral portion 82, and a tip 84. A first number of openings 86 extending through the first side 78 adjacent to the fluid channel 32 and located between the ends 88,90 of the crimping blade 76 can be configured to deliver fluid at a location between the ends of the stent. A second number of openings 92 disposed at or near the opposing ends of the fluid channel 32, in turn, can be configured to deliver fluid onto only the ends of the stent. In some embodiments, the size of the openings 92 disposed at or near the ends 88,90 can be slightly larger than the first number of openings 86 to permit more fluid to be ejected towards the ends of the stent. In some embodiments, the shape of the openings 92 disposed at or near the ends 88,90 can also differ from that of the openings 86, as shown. The differences in the size and/or shape of the openings may be used, for example, to spray more adhesive onto the ends of the stents for a stronger bond to the balloon of the balloon catheter. This may provide for more enhanced stent securement at the ends of the stent where the stent may be more likely to break off from the balloon during delivery. In other embodiments, the differences in the size and/or shape of the openings may be used to provide a thicker and/or additional coating onto the ends of the stents relative to the thickness and/or amount of coating applied to the central portion of the stent.

Figure 9:
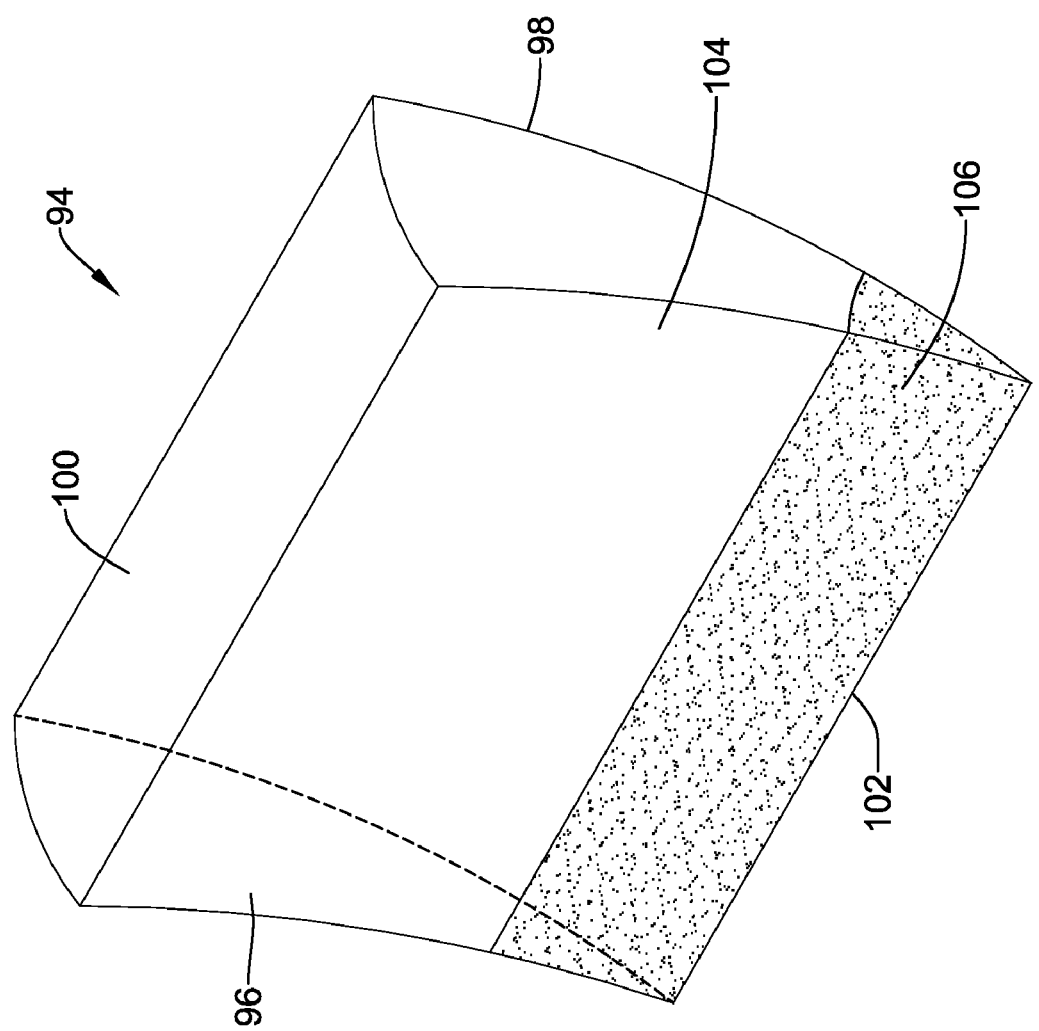
FIG. 9 is a perspective view showing an illustrative composite crimping blade.

FIG. 9 is a perspective view showing another illustrative crimping blade 94 having a composite tip along the length of the blade 94. The crimping blade 94 may be shaped similar to the crimping blade 14 depicted in FIG. 3, having a wedge shape defined by a first side 96, a second side 98, a peripheral portion 100, and a tip 102. In the illustrative embodiment depicted, the crimping blade 94 may have a first portion 104 constructed from a first material and a second portion 106 constructed from a second material, forming a blade 94 having a composite structure. In certain embodiments, for example, the second portion 106 of the composite crimping blade 94 can be formed from a material that, when contacted with the outer surface of the stent and/or stent delivery device, provides a layer or coating of adhesive onto the assembly that facilitates stent securement. Alternatively, and in other embodiments, the second portion 106 of the composite crimping blade 94 can be made from a polymeric material that, when contacted with the outer surface of the stent, provides a pharmaceutical and/or therapeutic agent or drug onto the stent assembly.

Referring now to FIGS. 10-13, an illustrative method of crimping and abluminally coating a stent assembly will now be described. As shown in a first view in FIG. 10, a stent 108 disposed onto the balloon 110 of a balloon delivery catheter 112 may be inserted into the crimping lumen 16 of the crimping apparatus 10 with the crimping blades 14 in a first (i.e. open) configuration. At this stage, the crimping blades 14 may be in a retracted state such that no radial forces are applied to the stent 108. Insertion of the stent 108 into the crimping lumen 16 can be accomplished, for example, via a loading channel, by a pushing rod, or by some other suitable insertion means.

The catheter 112 may be inserted into the crimping lumen 16 in a retracted configuration with the balloon 110 in a deflated state. Prior to or subsequent to insertion within the apparatus 10, the catheter 112 can be inserted into the interior lumen of the stent 108 such that the stent 108 is positioned over the balloon 110. The stent 108 may be positioned over the balloon 110, for example, by slipping the stent 108 over the balloon 110.

In some embodiments, the stent 108 can be releasably coupled to the balloon 110, and thus to the catheter 112, using an adhesive material. For example, an adhesive material having a melting point below that of the balloon 110 may be applied between the inner surface of the stent 108 and the outer surface of the balloon 110. An illustrative adhesive material may be Sorbitol or other biodegradable material. In some cases, the adhesive material may comprise a biocompatible material having a melting point below that of the balloon material (e.g. below 165° F.). The adhesive material may be dispersed in a fluid such as water to form a dilute solution, which may facilitate dispersion of the adhesive. The adhesive material may be applied between the inner surface of the stent and the outer surface of the balloon, for example, by introducing the material within a sheath. For example, a sheath made of a material such as polytetrafluoroethylene (PTFE) or the like may be positioned over both the stent 108 and the balloon 110. In some cases, a spray lubricant material such as glycerol can be used to reduce the frictional forces as the stent 108 is loaded onto the catheter 112 and is crimped thereto. The glycerol can be applied, for example, as part of an aqueous solution.

Figure 10:
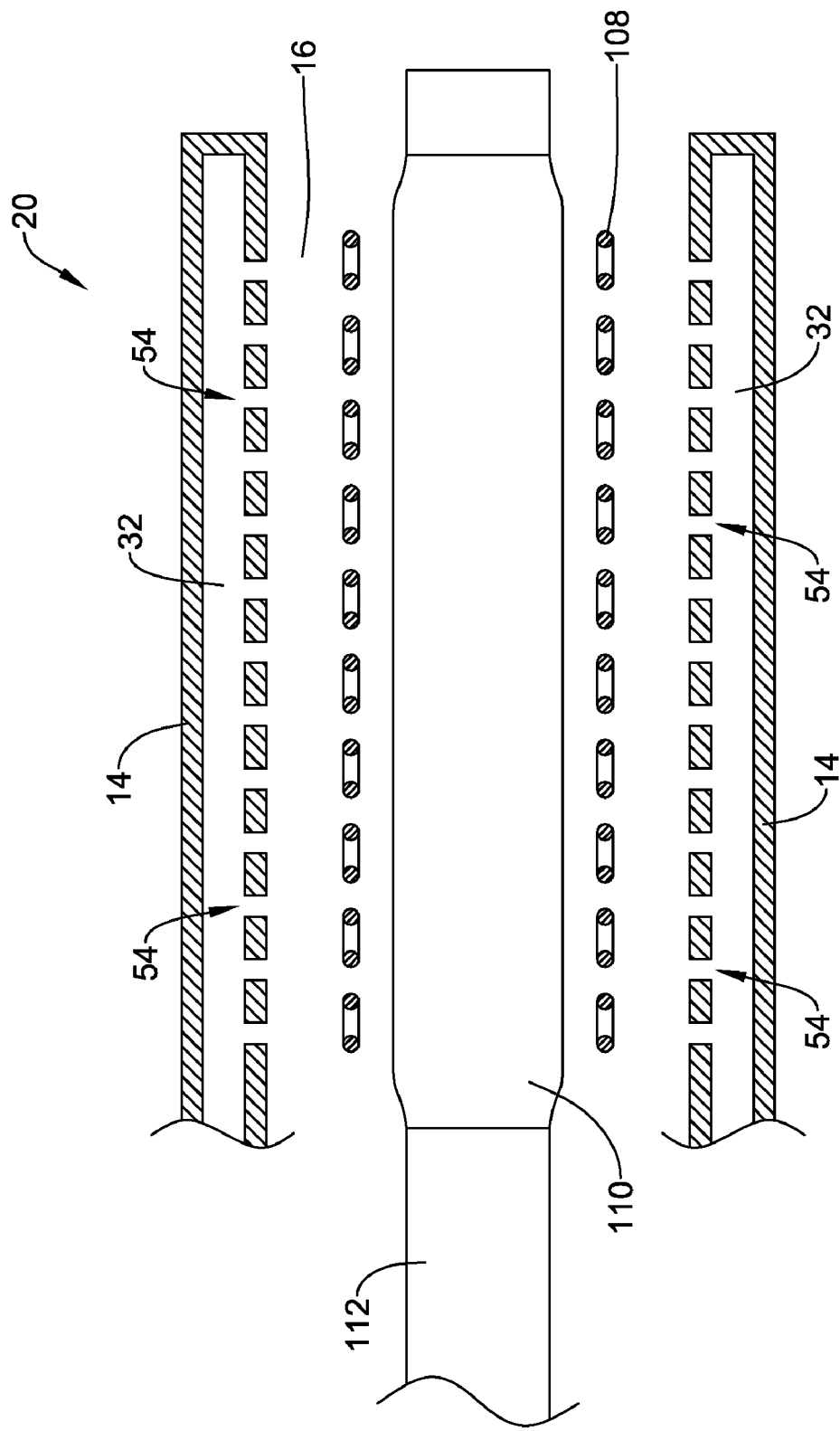
FIGS. 10-13 illustrate a method of crimping a stent onto a balloon of a stent delivery catheter and coating the stent on the balloon.
Figure 11:
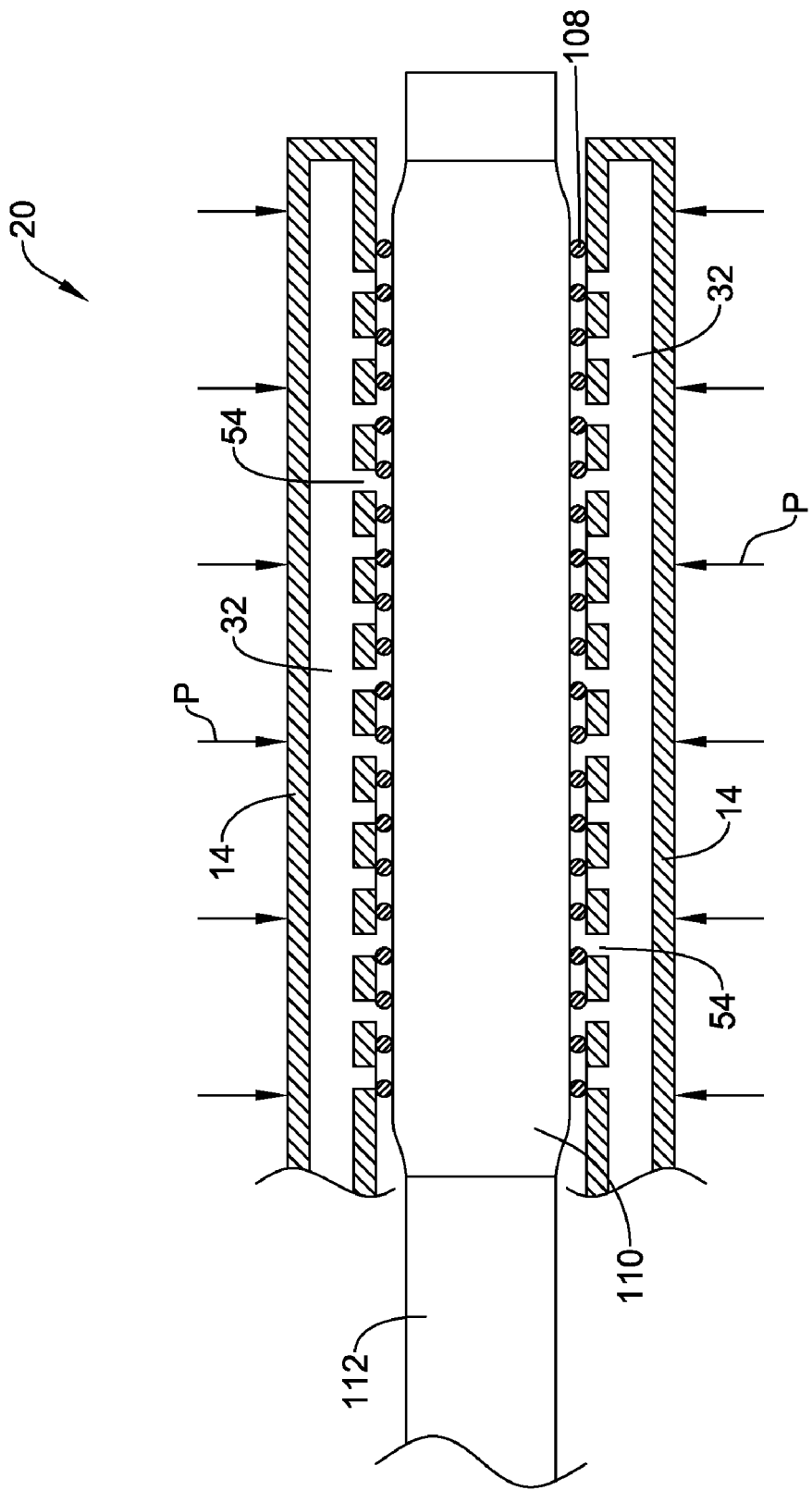

The balloon delivery catheter 112 may comprise any catheter known in the art that is appropriate for delivering a stent to a lesion site. In some embodiments, for example, the delivery catheter 112 may comprise a percutaneous transluminal coronary angioplasty (PTCA) balloon catheter capable of performing an angioplasty procedure. Other delivery devices are possible, however. The balloon 110 can be made from thermoplastic polymer such as polyvinyl chloride (PVC), polyolefins (e.g. polyethylene, polypropylene, etc.), polyester (e.g. polyethylene terephthalate), polyamide (e.g. nylon), polyurethane, ethylene-vinyl acetate, thermoplastic elastomers, or the like. Typically, the balloon 110 will have a length similar to, or in some cases slightly larger than, the axial length of the stent 108. The length and diameter of the balloon 108 may be selected based on the dimensions of the stent 108 to be delivered. Although the step depicted in FIG. 10 illustrates the insertion of the stent 108 and balloon delivery catheter 112 into the crimping lumen 16 as a single assembly, it should be understood that the stent 108 and balloon delivery catheter 112 can be inserted into the crimping apparatus 10 at different stages, if desired.

The stent 108 may have a generally cylindrical shape having a fenestrated structure for placement in a blood vessel, duct or lumen. The cylindrical body portion may be formed with a number of wire-like sections that are joined to one another at a number of interstices. The stent 108 may be made of a wide variety of biocompatible materials including, but not limited to, stainless steel, Nitinol, tantalum, ceramic, polyamides, polyolefins, and non-absorbable polyesters such as polyethylene terephthalate. One illustrative nonmetallic material is poly(ethylene oxide), which has a melting point between 140° F. and 160° F. In some embodiments, the stent 108 may be formed from a medical grade stainless steel with the outer surface being plated or otherwise including a coating of platinum to provide for improved visibility with a fluoroscope. The inside surface of the stent 108 may be smooth to reduce friction with the balloon material. The outer surface of the stent 108, in turn, may be relatively rough to prevent slippage of the stent 108 along the vessel surface during stent placement.

Once the stent 108 has been loaded onto the balloon delivery catheter 112 and the stent/balloon delivery catheter assembly is positioned within the crimping lumen 16 of the crimping apparatus 10, the crimping blades 14 may then be contracted radially inwardly to crimp the assembly. As shown in a subsequent step depicted generally in FIG. 1, for example, the extension of the blades 14 in a direction indicated generally by arrows P causes the blades 14 to engage the outer portion of the stent 108, producing a radially inwardly force that causes the tips 44 of the crimping blades 14 to come into contact with the stent 108 and compress or crimp the stent 108 about the balloon 110 such that the stent 108 is compressed or crimped to a smaller diameter around the balloon 110. In some techniques, it may be desirable to repeatedly crimp the stent 108 by slightly rotating the stent 108 and balloon delivery catheter 112 a few degrees and then applying a further crimping force to the assembly. For example, subsequent to a first crimping step illustrated in FIG. 11, the stent assembly can be rotated about 5 degrees, about 10 degrees, about 30 degrees, about 60 degrees, about 90 degrees, or about 180 degrees and crimped a second time. If desired, the amount of crimping force applied to the stent assembly can be measured with strain gauges attached to the blades 14. In other embodiments, other force measurement devices or means may be used.

Figure 12:
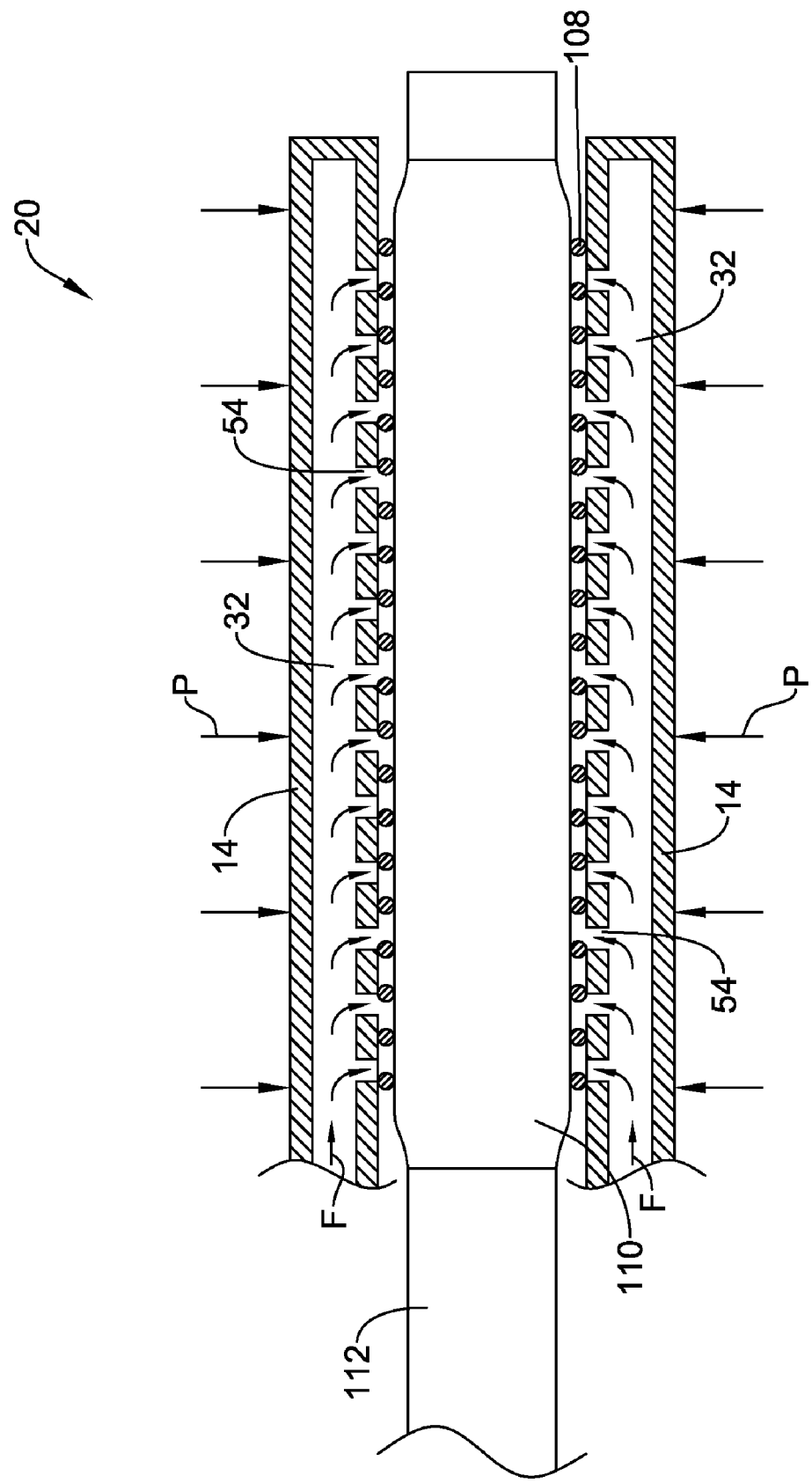

As shown in FIG. 12, as a crimping force is maintained on the stent 108 by the crimping apparatus 10, a pressurized fluid F may be expelled from the channel 32 through the openings 54 toward the stent 108 and/or balloon 110. The fluid F may form a coating on the stent 108 and/or balloon 110. Through such a coating process, the stent 108 may be abluminally coated with a coating. As used herein, "abluminally coated" is intended to refer to the stent 108 being coated on an exterior (i.e., radially outward surface of the stent 108) while an interior (i.e., radially inward surface of the stent 108) remains devoid of the coating.

Figure 13:
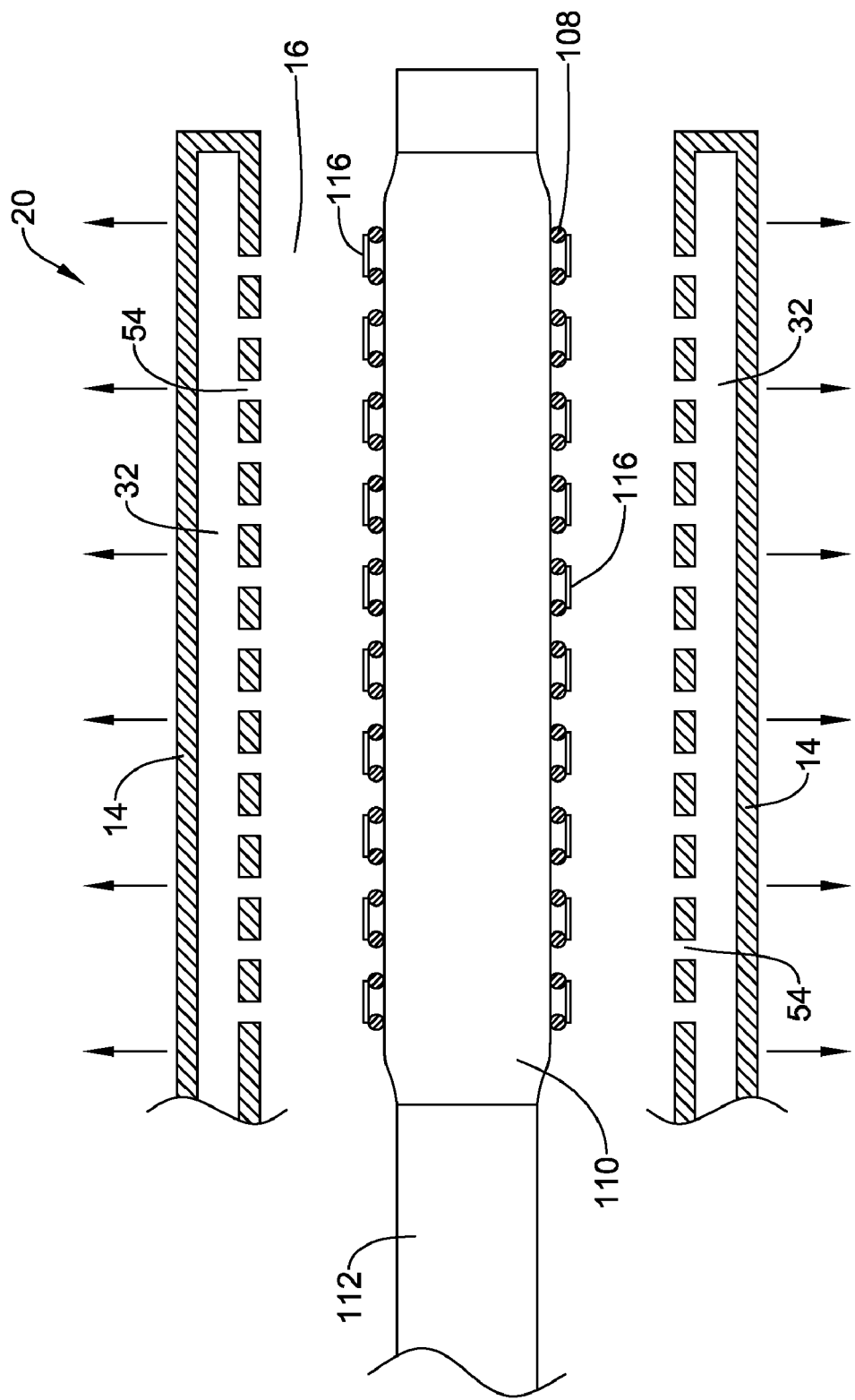

As shown in FIG. 13, once the stent 108 has been sufficiently crimped and coated, the crimping blades 14 may be retracted away from the stent delivery assembly to remove the stent delivery assembly from the crimping apparatus 10. The stent 108 is shown including a coating 116 disposed on the outer surface of the stent 108.

To coat the outer surface of the stent 108 and a portion of the catheter 112, pressurized fluid may be provided to the fluid channel 32, causing the fluid to be discharged through the orifices/openings 54 on the tip 44 of the crimping blade 14. In some embodiments, the entire outer surface of the stent 108 and the exposed portions of the balloon 110 can be coated by rotating the balloon delivery catheter 112 and attached stent 108 within the crimping lumen 16 while fluid F is discharged through the fluid openings 54. If desired, the balloon delivery catheter 112 may also be moved longitudinally within the crimping lumen 16. For example, the balloon delivery catheter 112 can be moved back and forth longitudinally within the crimping lumen 16 using a loading channel, or the like.

Figure 14A:
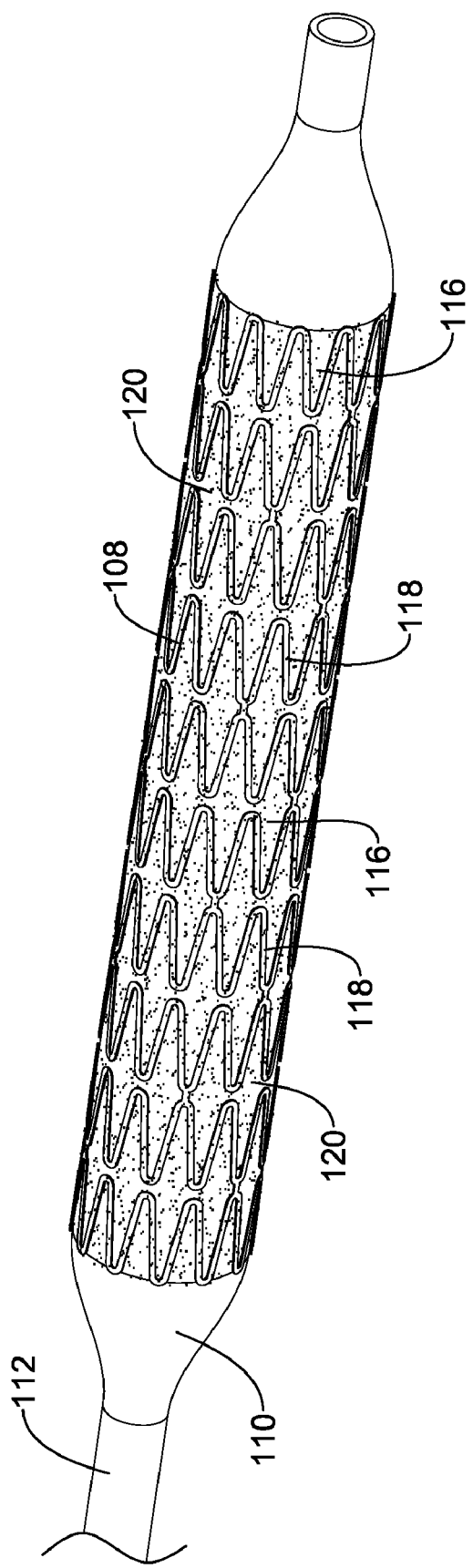
FIG. 14A is a perspective view showing a coated stent attached to a balloon delivery catheter.

FIG. 14A is a perspective view showing an illustrative balloon delivery catheter 112 and stent 108 having a coating 116 formed by the method described above with respect to FIGS. 10-13. As shown in FIG. 14A, the coating 116 may be formed on the outer surfaces of the stent wire 118 segments and on the exposed portions of the balloon 110 located within the interstices or spaces 120 between the stent wires 118. Thus, as can be seen, the stent 108 may be abluminally coated with a coating 116, such that the outer surface of the stent 108 may include a coating 116, while the inner surface of the stent 108 (i.e., the surface of the stent contacting the balloon 110), may remain uncoated.

In other embodiments, coating the stent 108 without rotating the balloon delivery catheter 112 and attached stent 108 within the crimping lumen 16 may result in longitudinal stripes of the coating 116 being applied, with adjacent longitudinal portions remaining uncoated.

Figure 14B:
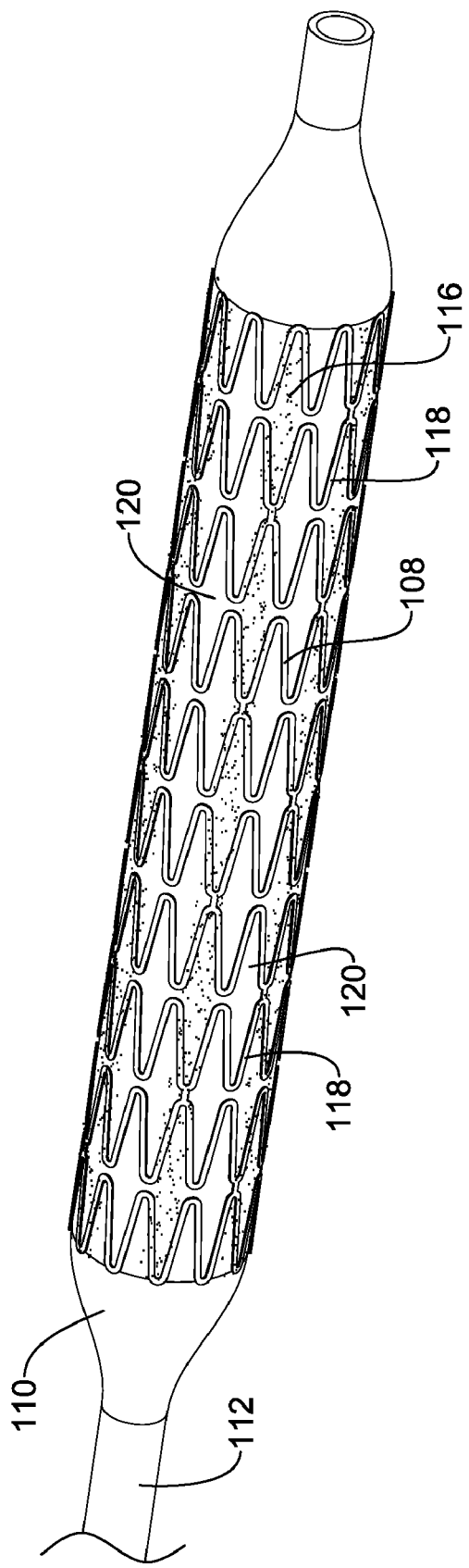
FIG. 14B is a perspective view showing another embodiment of a coated stent attached to a balloon delivery catheter.

FIG. 14B is a perspective view showing an illustrative balloon delivery catheter 112 and stent 108 having a longitudinal striped coating 116 formed with the crimping apparatus 10. As shown in FIG. 14B, the coating 116 may be formed in discrete longitudinal stripes on the outer surfaces of the stent wire 118 segments and on the exposed portions of the balloon 110 located within the interstices or spaces 120 between the stent wires 118 with adjacent longitudinal portions remaining uncoated. Thus, as can be seen, the stent 108 may be abluminally coated with a striped coating 116, such that the outer surface of the stent 108 may include discrete longitudinal sections having a coating 116 adjacent longitudinal sections remaining uncoated, while the inner surface of the stent 108 (i.e., the surface of the stent contacting the balloon 110), may remain uncoated.

A variety of stent coatings and compositions may be placed onto the stent 108 may include a therapeutic agent for preventing intimal thickening, smooth muscle tissue proliferation, restenosis, inflammation, coagulation, and/or other conditions at the treatment site. An example drug coating may comprise Rapamycin and/or Heparin. Examples of other drugs that can be used are described in U.S. Pat. No. 7,225,518, which is incorporated herein by reference in its entirety. The mechanism for delivery of the therapeutic agent can be through diffusion of the agent through either a bulk polymer or through pores in the polymeric structure, or by erosion of a biodegradable coating such as in the illustrative composite tip 94 in FIG. 9. In some embodiments, one or more of the crimping blades 14 can be configured to provide other materials onto the stent and balloon delivery catheter. For example, in some embodiments the crimping blades 14 can be configured to deliver a bonding agent that improves adhesive retention of the stent 108 to the balloon 110, or a lubricious material to aid in crossing a lesion within a blood vessel.

If an adhesive is used to help secure the stent 108 to the balloon, the adhesive material forms weak adhesion points at the stent-balloon interface, forming a bond between the stent 108 and the balloon 110. During delivery, this bond may retain the stent 108 to the balloon 110 while permitting the stent 108 to be later released from the balloon 110 following inflation and deflation of the balloon 110 at the treatment site during stenting.

Figure 15:
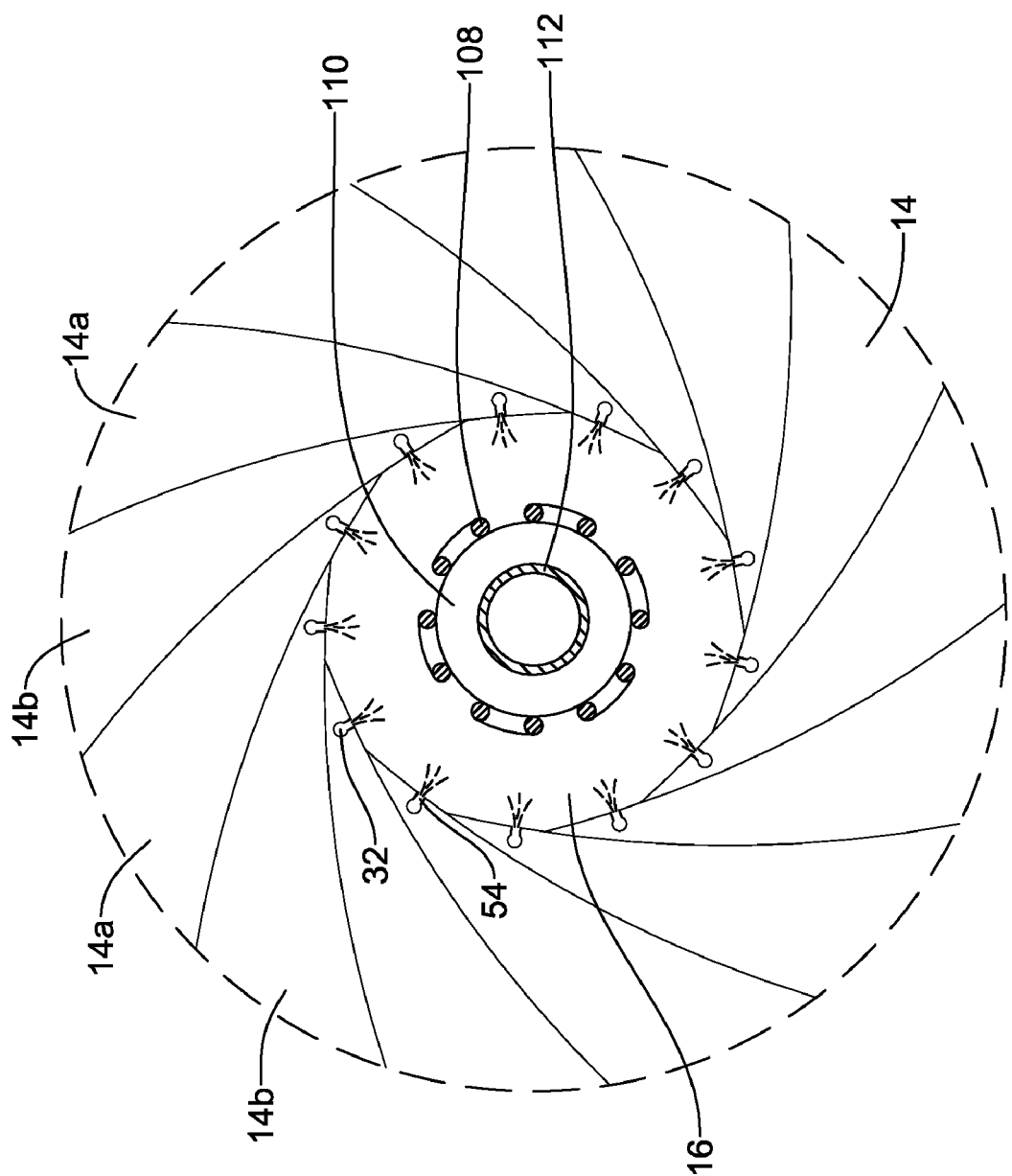
FIG. 15 is a cross-sectional view of a crimping apparatus including a stent and balloon delivery catheter positioned therein.

In an alternative embodiment, once the uncoated stent 108 has been secured (e.g., crimped) to the balloon delivery catheter 112, the crimping blades 14 may be retracted away from the assembly a short distance, forming a small gap between the outer surfaces of the stent 108 and the blades 14. In some embodiments, a coating may be applied to the stent 108 and/or balloon 110 with the crimping blades 14 of the crimping apparatus 10 retracted away from and not in contact with the stent 108. As shown in FIG. 15, either prior to or subsequent crimping the stent 108 onto the balloon 110, fluid F may be discharged through the openings 54 of the crimping blades 14 toward the stent 108, while the crimping blades 14 are retracted away from the stent 108. Such a process may be found to more completely cover the stent 108 and/or balloon 110 with a coating, if desired.

In some embodiments, the crimping blades 14 may be heated to an elevated temperature during the crimping process. In some instances, heat emitting from the heated crimping blades 14 may warm the fluid F to increase the flowability and/or viscosity of the fluid F to facilitate application of the fluid F on the stent 108. In some instances, heat emitting from the heated crimping blades 14 may help cure, solidify, bond, adhere, activate, preserve, convert, or otherwise affect the coating applied on the stent 108.

Furthermore, in some embodiments, the crimping apparatus 10 may include a first subset of crimping blades 14 including one or more crimping blades 14a, and a second subset of crimping blades 14 including one or more crimping blades 14b. In some embodiments, the crimping apparatus 10 may include additional subsets of crimping blades 14 if desired. The first subset of crimping blades 14a may be configured to discharge a first fluid $F_1$ while the second subset of crimping blades 14b may be configured to discharge a second fluid $F_2$. If the crimping apparatus 10 includes a third or additional subset of crimping blades, the third subset of crimping blades may be configured to discharge a third fluid.

Thus, during a stent coating process using the crimping apparatus 10, multiple coatings may be applied to the stent 108 and/or balloon 110, as desired. For example, a first coating layer may be applied to the stent 108, followed by a second coating layer overlying the first coating layer. In some embodiments, a third or additional coating layer may subsequently be applied to the stent overlying both the first and second coating layers.

Thus, in some embodiments, a first coating layer, which may be an adhesive or bonding layer may be overlaid with a second coating layer, which may be a top coat. A third coating layer, which may include a therapeutic agent, may be disposed over the second coating layer. Alternatively, in some embodiments, the first coating layer may include a therapeutic agent, and the second coating layer disposed over the first coating layer may be applied to delay the release of the therapeutic agent included in the first coating layer. Or, the second coating layer may include a different therapeutic agent. Thus, the layering of coatings may be used to stage release of a therapeutic agent or to control release of different agents placed in different layers.

Figure 16B:
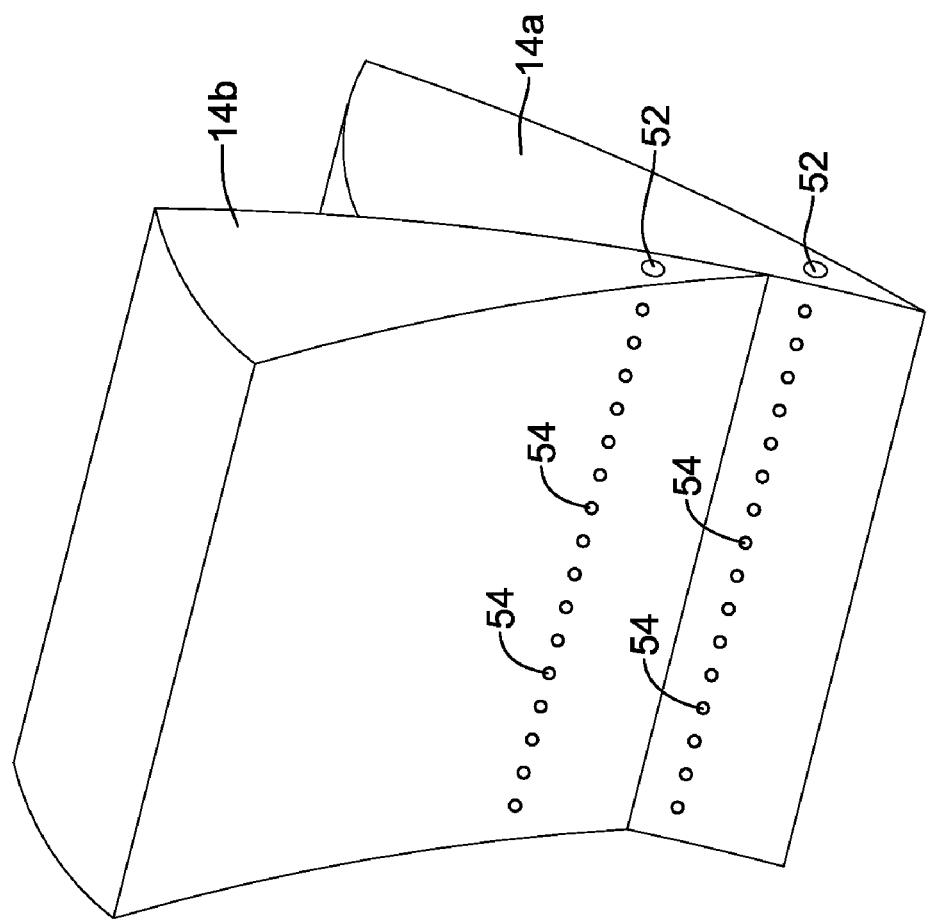
FIGS. 16A and 16B illustrate the crimping blades of a crimping apparatus in a radially retracted position.
Figure 16A:
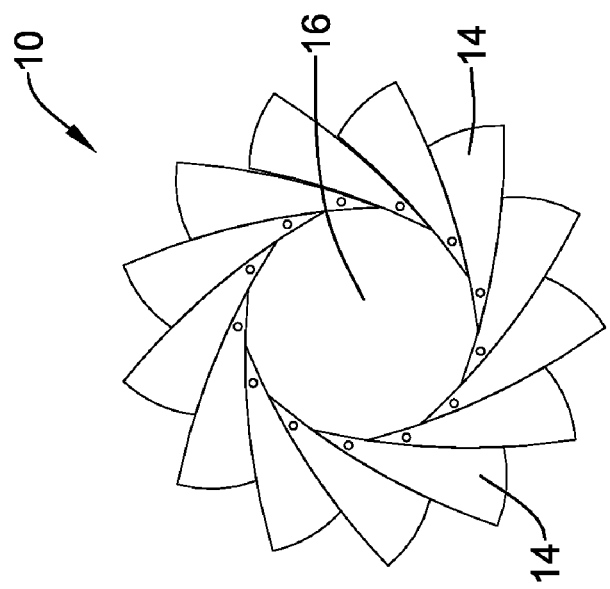
Figure 17B:
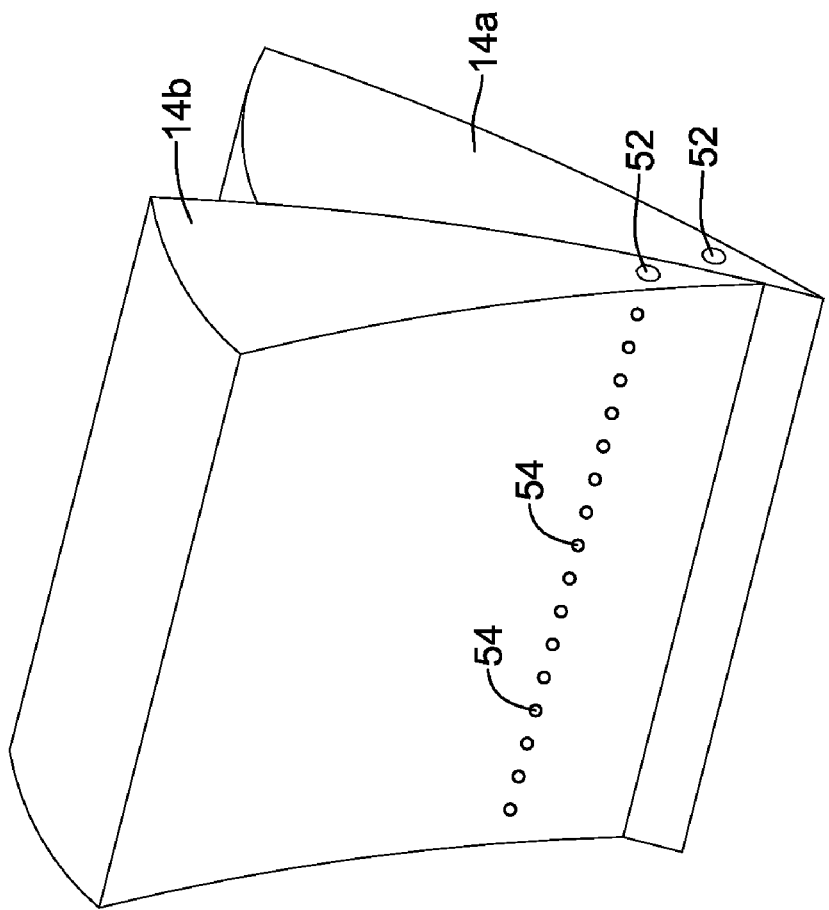
FIGS. 17A and 17B illustrate the crimping blades of a crimping apparatus in a radially contracted position.
Figure 17A:
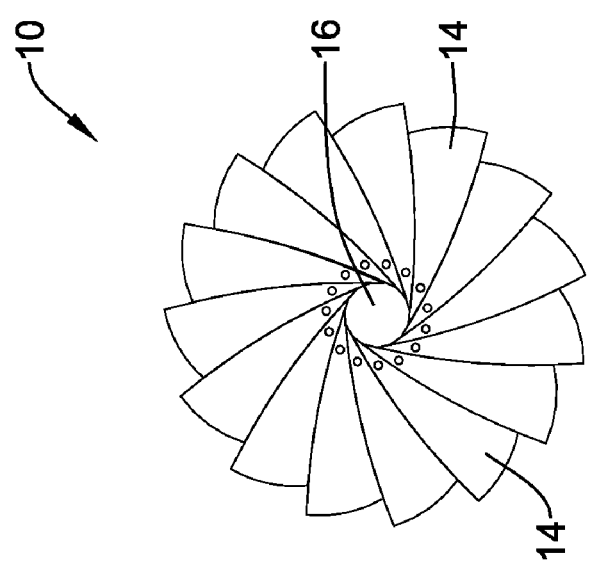
Figure 18:
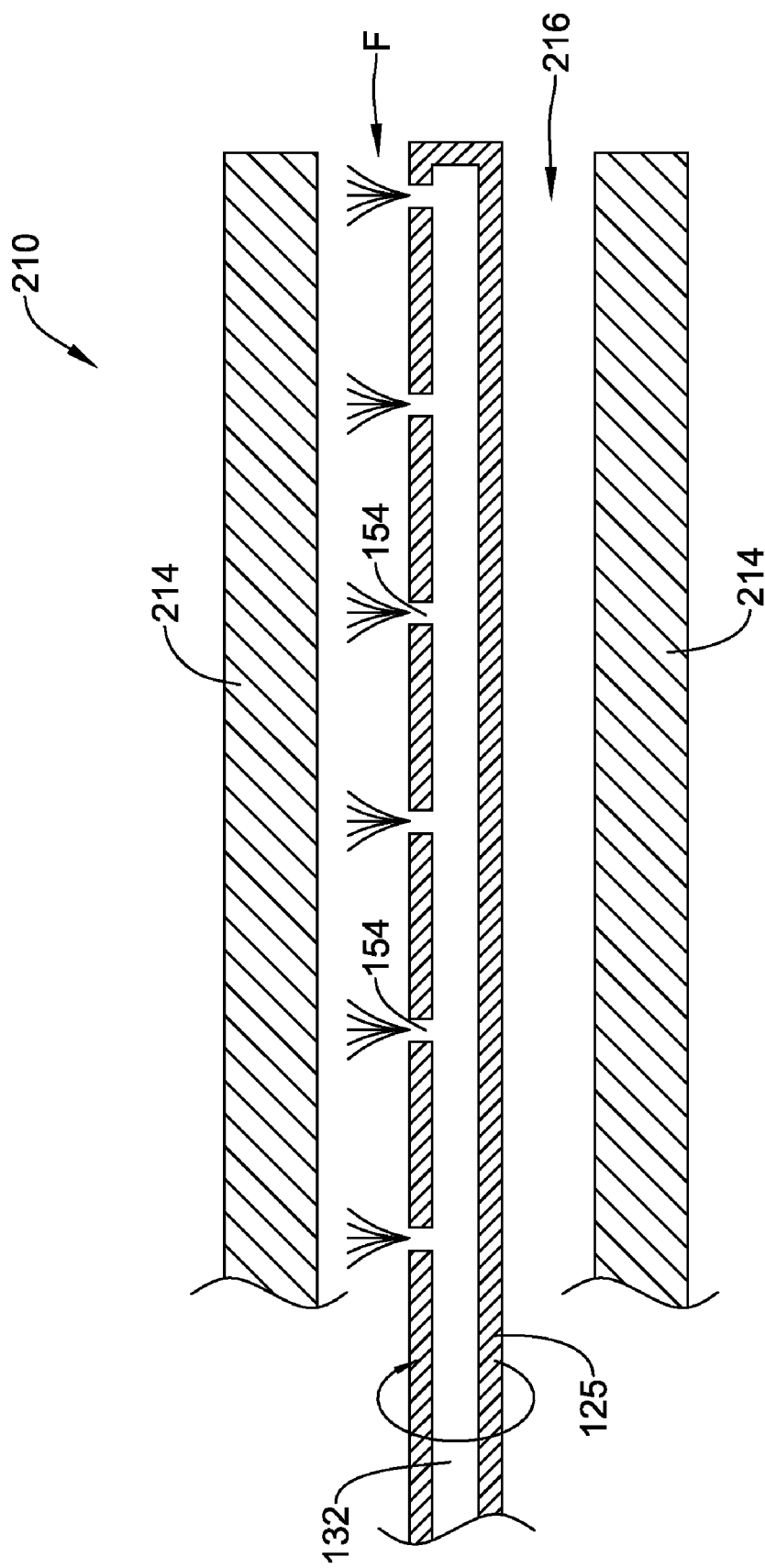
FIGS. 18-21 illustrate another method of crimping a stent onto a balloon of a stent delivery catheter and coating the stent.

FIGS. 16A and 17A are end views of a stent crimping apparatus 10 including a plurality of crimping blades 14 as described above, positioned to define a central crimping lumen 16. The crimping lumen 16 shown in FIG. 16A has a first diameter and the crimping lumen 16 shown in FIG. 17A has a second diameter less than the first diameter of the crimping lumen 16 shown in FIG. 16A. As described above, the diameter of the crimping lumen 16 may be changed by retracting and/or contracting the crimping blades 14 during a crimping procedure.

FIGS. 16B and 17B are perspective views of the relationship of two crimping blades 14 of the crimping apparatus 10 relative to the diameter of the crimping lumen 16. It is to be understood that, although only two crimping blades 14 are shown, the additional crimping blades 14 of the crimping apparatus 10 may interact with adjacent crimping blades in a similar fashion. As shown in FIG. 16B, when the crimping lumen 16 is of a sufficient enlarged diameter, the openings 54 of a first crimping blade 14a may not be covered or blocked by an adjacent second crimping blade 14b. However, as shown in FIG. 17B, when the crimping lumen 16 is reduced in dimension, the openings 54 of the first crimping blade 14a may be covered or blocked by the second, adjacent crimping blade 14b. It should be understood that, although not shown, during operation the openings 54 of the second crimping blade 14b would additionally be covered or blocked with an additional adjacent crimping blade (not shown). Thus, when the crimping lumen 16 is of the size shown in FIG. 17A, the openings 54 of each of the blades 14 of the crimping apparatus 10 may be covered or blocked by an adjacent one of the blades 14, and when the crimping lumen 16 is of the size shown in FIG. 16A, the openings 54 of each of the blades 14 of the crimping apparatus 10 may be uncovered or not blocked by an adjacent one of the blades 14.

When the openings 54 of a crimping blade 14 are covered or blocked by an adjacent crimping blade 14, a fluid F located in the channel 32 of the blades 14 will be prevented from being expelled from the openings 54. However, when the openings 54 of a crimping blade 14 are not covered or blocked by an adjacent crimping blade 14, the fluid F located in the channel 32 of the blades 14 will be permitted to be expelled from the openings 54.

Thus, for example, during operation a stent may be crimped onto a balloon of a catheter by placing the stent and balloon into the central opening 16 and contracting the crimping blades 14 of the crimping apparatus 10 to the crimping lumen 16 diameter shown in FIG. 17A. At this diameter, a fluid F is prevented from being expelled from the openings 54, as the openings 54 are covered or blocked by adjacent crimping blades 14. After the crimping step has been performed, the crimping blades 14 may be retracted such that the crimping lumen 16 is enlarged to the diameter shown in FIG. 16A. At this diameter, a fluid F may be discharged from the openings 54 of the crimping blades 14 in order to abluminally coat the stent and/or balloon subsequent to the crimping step.

In other embodiments, the stent and/or balloon may be coated with the fluid F discharged from the openings 54 of the crimping blades 14 prior to crimping the stent onto the balloon, while the crimping lumen 16 is enlarged to the diameter shown in FIG. 16A. Thus, in such embodiments, once the fluid F is discharged from the openings 54 of the crimping blades 14, the crimping blades 14 of the crimping apparatus 10 may be contracted such that the crimping lumen 16 is of the size shown in FIG. 17A, to thus crimp a stent onto a balloon after coating the stent and/or balloon with a fluid F discharged from the openings 54 of the crimping blades 14.

FIGS. 18-21 are several side views showing another illustrative method of crimping and abluminally coating a stent assembly. As shown in a first view in FIG. 18, a coating apparatus 125 may be inserted into the crimping lumen 216 of a crimping apparatus 210. The coating apparatus 125 may include one or more, or a plurality of openings 154 in fluid communication with a lumen 132 of the coating apparatus 125. In some embodiments, the openings 154 may include nozzles or valves similar to the nozzles 45 or valves 49 of FIGS. 4B and 4C, or another means of controlling fluid discharge from the lumen 132 of the coating apparatus 125 through the openings 154.

With the coating apparatus 125 positioned in the crimping lumen 216 of the crimping apparatus 210, a fluid F may be discharged from the coating apparatus 125 to coat the inner surface of the crimping blades 214 forming the crimping lumen 216 of the crimping apparatus 210. In some embodiments, it may be desirable to rotate the coating apparatus 125 (as shown by the arrow of rotation of FIG. 17) in order to more fully coat the entire inner surface of the crimping lumen 216.

Figure 19:
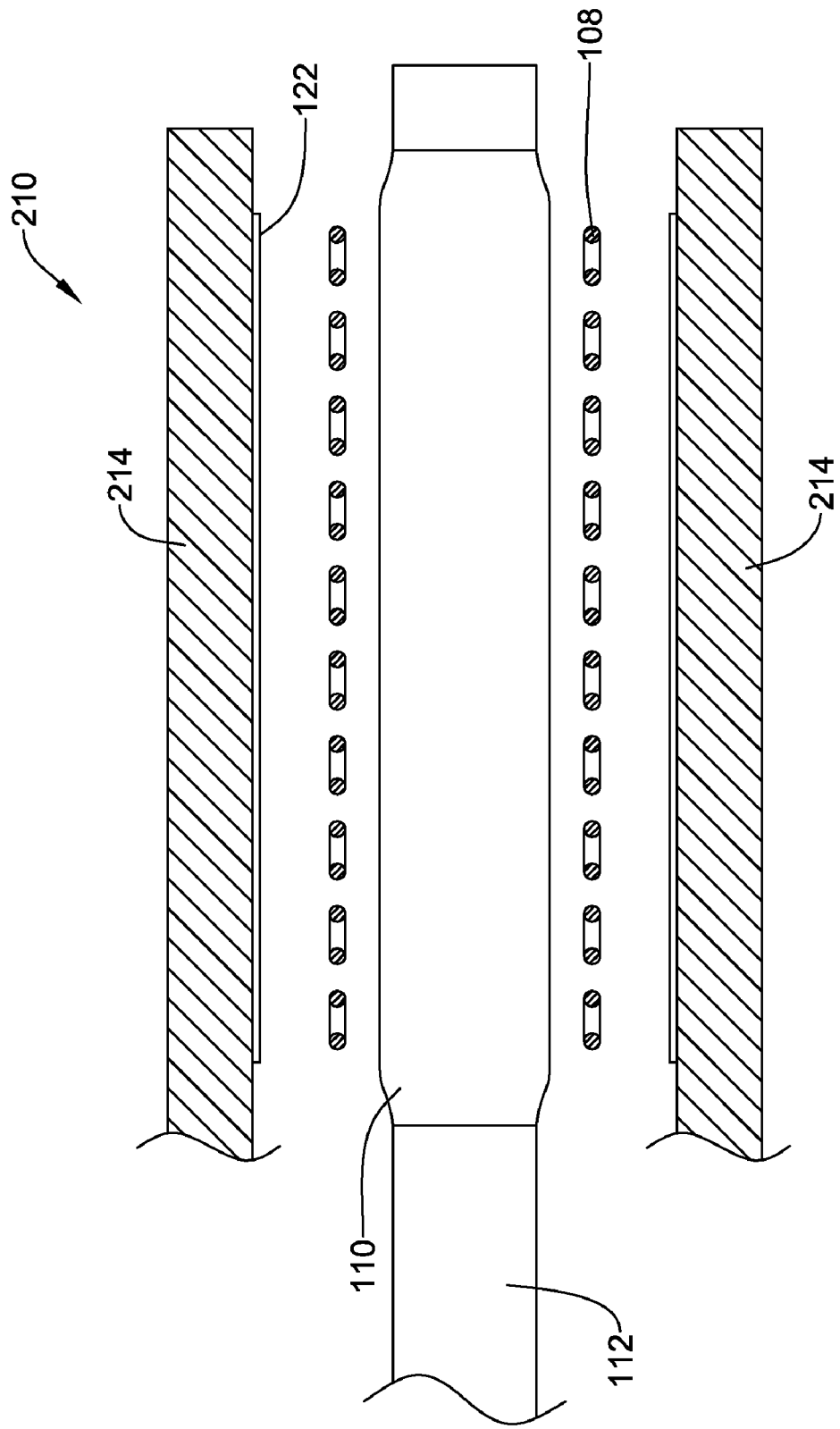

As shown in FIG. 19, once a desired amount of a coating 122 is applied to the inner surface of the crimping lumen 216, the coating apparatus 125 may be removed and a stent 108 and/or balloon 110 of a balloon catheter 112 may placed within the crimping lumen 216 of the crimping apparatus 210 with the crimping blades 214 in a first (i.e. open) configuration. At this stage, the crimping blades 214 may be in a retracted state such that no radial forces are applied to the stent 108. It is noted that the stent 108 may be loaded onto the balloon 110 of the balloon catheter 112 either before or after placing the stent 108 within the crimping lumen 216 of the crimping apparatus 210.

Figure 20:
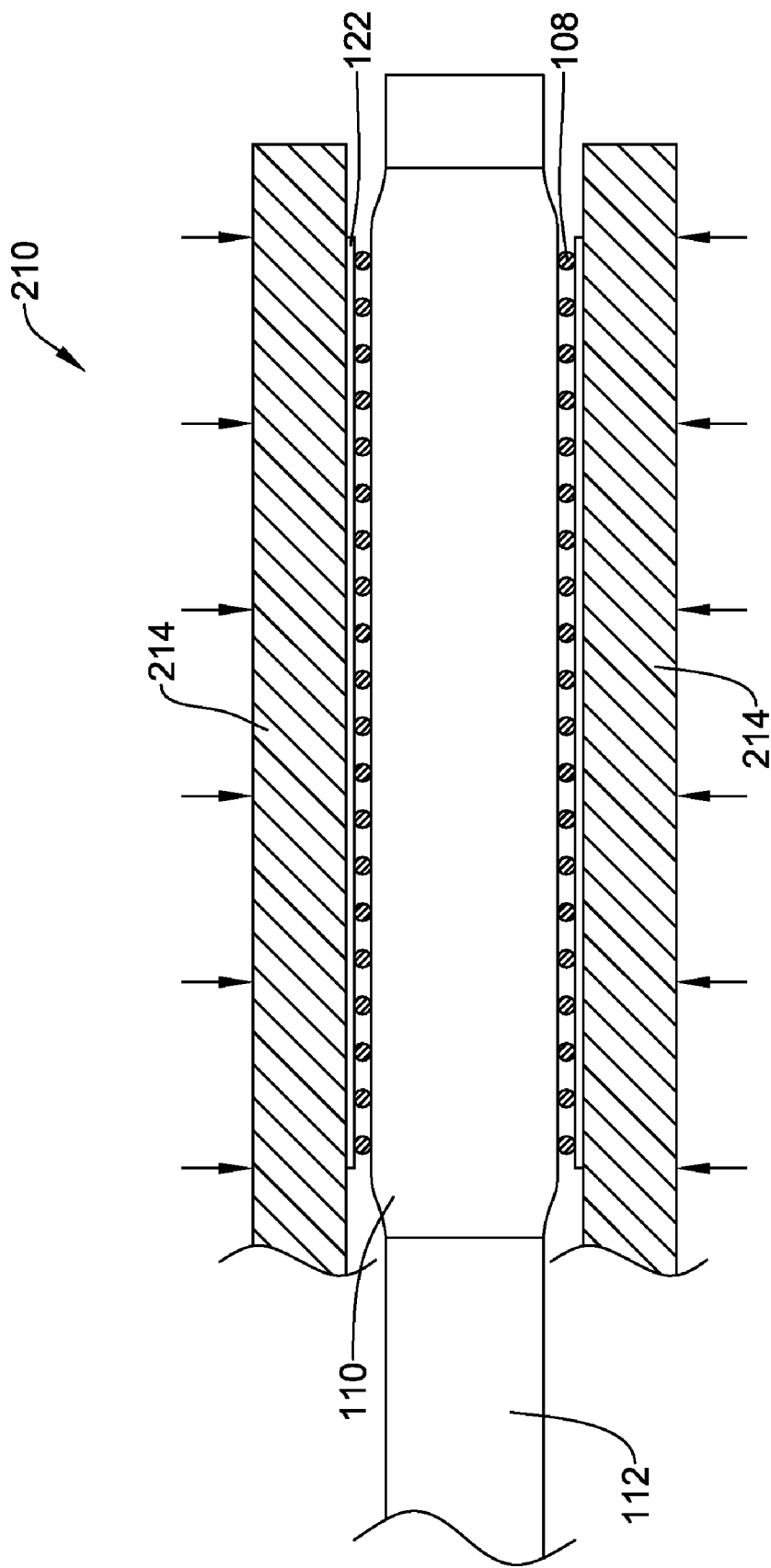

The crimping blades 214 of the crimping apparatus 210 may then be contracted around the stent 108 as shown in FIG. 20, exerting a radially inward force on the stent 108 to thereby compress and crimp the stent 108 around the balloon 110. The crimping force may be maintained for a desired duration of time to crimp the stent 108 onto the balloon 110. In some techniques, it may be desirable to repeatedly crimp the stent 108 by slightly rotating the stent 108 and balloon delivery catheter 112 a few degrees and then applying a further crimping force to the assembly. For example, subsequent to a first crimping step illustrated in FIG. 20, the stent assembly can be rotated about 5 degrees, about 10 degrees, about 30 degrees, about 60 degrees, about 90 degrees, or about 180 degrees, and crimped a second time.

As the stent 108 is being crimped, the coating 122, or a portion thereof, applied to the interior of the crimping lumen 216 may be transferred to the outer surface of the stent 108, thus abluminally coating the stent 108 with a coating 124.

Figure 21:
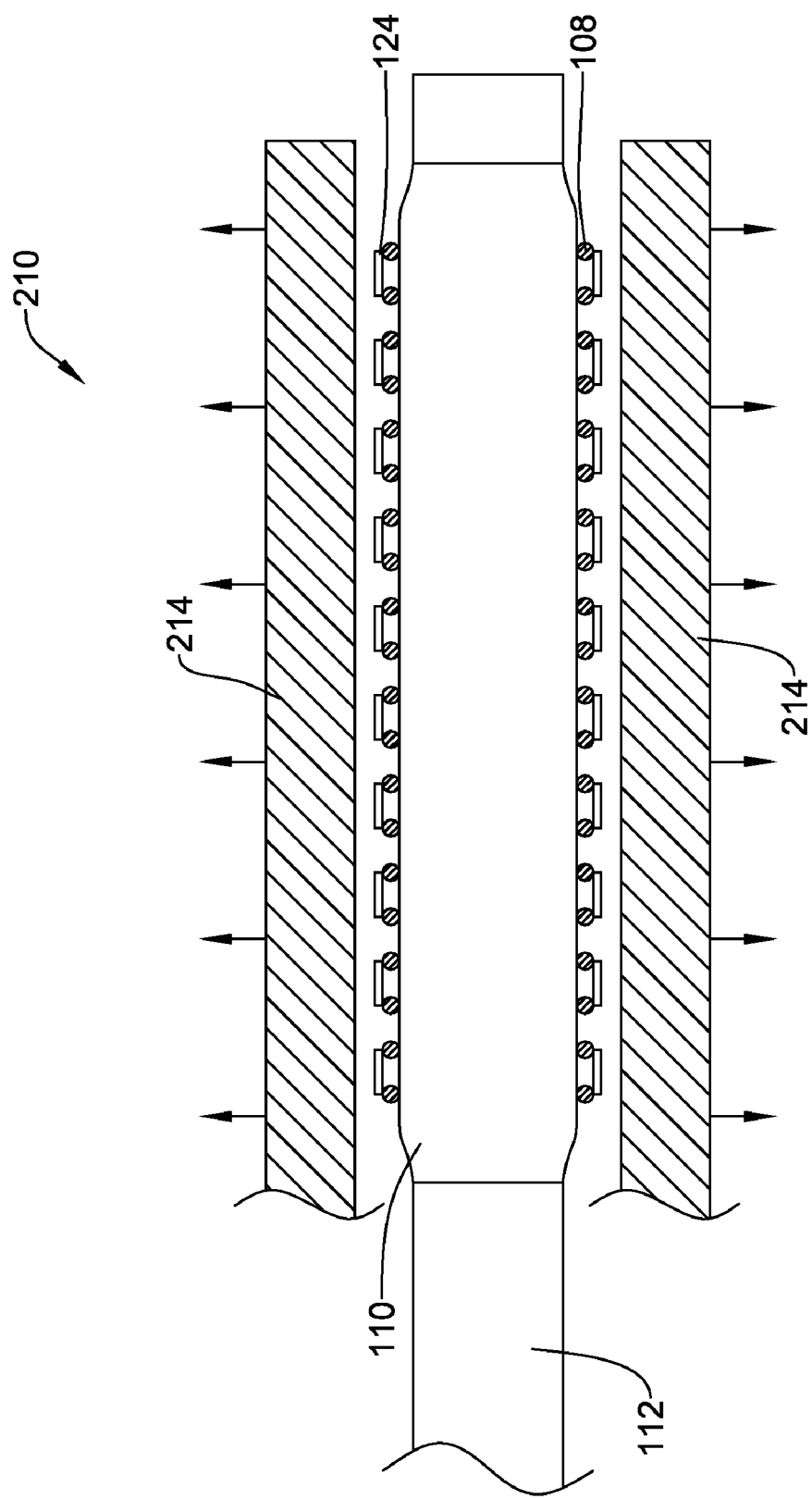

As shown in FIG. 21, once the stent 108 has been sufficiently crimped and coated with the coating 124, the crimping blades 14 may be retracted away from the stent delivery assembly to remove the stent delivery assembly from the crimping apparatus 10. The stent 108 is shown including a coating 124 disposed on the outer surface of the stent 108 as a result of the stent 108 contacting the coating 122 applied to the interior of the crimping lumen 216.

Having thus described the several embodiments of the present invention, those of skill in the art will readily appreciate that other embodiments may be made and used which fall within the scope of the claims attached hereto. It will be understood that this disclosure is, in many respects, only illustrative. Changes can be made with respect to various elements described herein without exceeding the scope of the invention.

What is claimed is:

1. A method of crimping and coating a stent on a stent delivery assembly, comprising the steps of:

providing a crimping apparatus including a plurality of crimping blades positioned in a radial array and collectively forming a central crimping lumen, the plurality of crimping blades radially movable to alter the diameter of the central crimping lumen, one or more of the crimping blades including a fluid channel and one or more openings in fluid communication with the fluid channel;

positioning a balloon of a balloon catheter and a stent surrounding a portion of the balloon in the crimping lumen of the crimping apparatus;

radially contracting the plurality of crimping blades toward the stent to thereby crimp the stent onto the balloon;

coating at least a portion of the stent by discharging a fluid into the crimping lumen and into contact with the stent from the one or more openings;

radially retracting the plurality of crimping blades away from the stent; and removing the balloon and crimped stent from the crimping lumen of the crimping apparatus.

2. The method of claim 1, wherein the step of coating at least a portion of the stent is performed while the plurality of crimping blades are radially contracted toward the stent.

3. The method of claim 1, wherein the step of coating at least a portion of the stent is performed prior to radially contracting the plurality of crimping blades toward the stent.

4. The method of claim 1, wherein the step of coating at least a portion of the stent is performed subsequent to radially retracting the plurality of crimping blades away from the stent.

5. The method of claim 1, wherein a first subset of the plurality of crimping blades each include a fluid channel in fluid communication with one or more openings and a second subset of the plurality of crimping blades include a fluid channel in fluid communication with one or more openings;

wherein the step of coating at least a portion of the stent includes discharging a first fluid through the openings of the first subset of crimping blades, and discharging a second fluid through the openings of the second subset of crimping blades.

6. The method of claim 5, wherein the first fluid forms a first coating layer on the stent and the second fluid forms a second coating layer overlaying the first coating layer.

7. The method of claim 1, further comprising the step of rotating the stent and balloon within the crimping lumen during the coating step.

8. The method of claim 1, wherein the coating step results in the stent having one or more longitudinal stripes of coating adjacent one or more uncoated longitudinal portions.

9. The method of claim 1, wherein the fluid is an adhesive, and wherein the adhesive bonds the stent to the balloon to help retain the stent onto the balloon.

10. A method of crimping and coating a stent on a stent delivery assembly, comprising the steps of:

providing a crimping apparatus including a plurality of crimping blades positioned in a radial array and collectively forming a central crimping lumen, the plurality of crimping blades radially movable to alter the diameter of the central crimping lumen;

applying a coating to the central crimping lumen of the crimping apparatus;

positioning a balloon of a balloon catheter and a stent surrounding a portion of the balloon in the crimping lumen of the crimping apparatus;

radially contracting the plurality of crimping blades toward the stent to thereby crimp the stent onto the balloon, wherein at least a portion of the coating is applied to the stent;

radially retracting the plurality of crimping blades away from the stent; and removing the balloon and crimped stent from the crimping lumen of the crimping apparatus.

11. The method of claim 10, wherein the step of applying a coating to the central crimping lumen includes inserting a fluid applicator into the central crimping lumen and discharging a fluid from the fluid applicator.

12. The method of claim 11, further comprising the step of rotating the fluid applicator within the central crimping lumen.

13. The method of claim 10, wherein the stent is abluminally coated.

* * * * *